(12) United States Patent
Vo-Dinh

(10) Patent No.: US 7,267,948 B2
(45) Date of Patent: Sep. 11, 2007

(54) SERS DIAGNOSTIC PLATFORMS, METHODS AND SYSTEMS MICROARRAYS, BIOSENSORS AND BIOCHIPS

(75) Inventor: Tuan Vo-Dinh, Knoxville, TN (US)

(73) Assignee: Ut-Battelle, LLC, Oak Ridge, TN (US)

( * ) Notice: Subject to any disclaimer, the term of this patent is extended or adjusted under 35 U.S.C. 154(b) by 141 days.

(21) Appl. No.: 10/229,600

(22) Filed: Aug. 28, 2002

(65) Prior Publication Data

US 2003/0059820 A1    Mar. 27, 2003

Related U.S. Application Data

(63) Continuation-in-part of application No. 09/890,047, filed on Jul. 25, 2001, and a continuation-in-part of application No. 09/771,530, filed on Jan. 29, 2001, now Pat. No. 6,448,064, which is a continuation-in-part of application No. 09/236,758, filed on Jan. 25, 1999, which is a continuation of application No. 08/979,672, filed on Nov. 26, 1997, now Pat. No. 6,197,503.

(51) Int. Cl.
C12Q 1/68 (2006.01)
C12M 1/34 (2006.01)

(52) U.S. Cl. .................. 435/6; 435/287.2; 435/91.1

(58) Field of Classification Search ................. 204/299; 422/68.1, 82.05; 435/6, 91.2; 436/525
See application file for complete search history.

(56) References Cited

U.S. PATENT DOCUMENTS

| 5,174,677 A | 12/1992 | Doolin et al. |
| 5,376,252 A * | 12/1994 | Ekstrom et al. ............ 204/603 |
| 5,376,556 A * | 12/1994 | Tarcha et al. ............... 436/525 |
| 5,690,894 A * | 11/1997 | Pinkel et al. .............. 422/68.1 |
| 5,721,102 A | 2/1998 | Vo-Dinh |
| 5,783,389 A | 7/1998 | Vo-Dinh |
| 5,814,516 A | 9/1998 | Vo-Dinh |
| 5,849,486 A * | 12/1998 | Heller et al. .................... 435/6 |
| 6,197,503 B1 | 3/2001 | Vo-Dinh et al. |
| 6,331,274 B1 | 12/2001 | Ackley et al. |
| 6,406,845 B1 * | 6/2002 | Walt et al. ...................... 435/6 |

OTHER PUBLICATIONS

Vo-Finh et al. Surface-enhanced gaman gene probes. 1994. Analytical Chemistry vol. 66:3379-3383.*
Vo-Dinh et al. Journal of Raman Spectroscopy vol. 30:785-793. 1999.*
Vo-Dinh. Sensors and Actuators B. 1998 pp. 1-8.*
Stokes et al. Fresenius' Journal of Analytical Chemistry. vol. 369:295-301. Abstract only. 2001.*
Kumar et al., "Monitoring of oligonucleotide hybridization using light-addressable potentiometric and evanescent wave florescence sensing," Materials Science and Engineering, C1: 187-192, 1994.

Eggers et al., "A Microchip for Quantitative Detection of Molecules Utilizing Luminescent and Radioisotope Reporter Groups", BioTechiques, 17:516-524, 1994.
Schena et al., "Quantitative Monitoring of Gene Expression Patterns with a Complementary DNA Microarray," Science, 270: 467-470, 1995.
Piunno et al., "Fiber optic biosensor for fluorimetric detection of DNA hybridization," Analytica Chimica Acta, 288:205-214, 1994.
Vo-Dinh et al., "Surface-Enhanced Raman Gene Probes," Anal. Chem., 66:3379-3383, 1994.
Stevenson et al., "Synchronous Luminescence: A New Detection Technique for Multiple Fluorescent Probes Used for DNA Sequencing," BioTechniques, 16: 1104-1110, 1994.
Isola et al., "Development of a Genosensor for *Mycobacterium tuberculosis*," SPIE. 2676: 228-240, 1996.
Alarie et al., "Intensified Charge Coupled Device-Based Fiber-Optic Monitor for Rapid Remote Surface-Enhanced Raman Scattering Sensing," Applied Spectroscopy, 46: 1608-1612, 1992.
Vo-Dinh et al., "Antibody-Based Fiberoptics Biosensor for the Carcinogen Benzo(a)pyrene," Applied Spectroscopy, 41: 735-738, 1987.
Saiki et al., "Primer-Directed Enzymatic Amplification DNA with a Thermostable DNA Polymerase," Science, 239: 487-491, 1988.
Graham et al., "Gene probe assays on a fibre-optic evanescent wave biosensor," Biosensors & Bioelectronics, 7: 487-493, 1992.
Vo-Dinh et al., "Development of a DNA Biochip for Gene Diagnosis ," Biomedical Sensing and Imaging Technologies, R. Lieberman et al., Eds., SPIE Publishers, Bellingham, WA, 1998 (in Press).
Vo-Dinh, T., "Development of a DNA biochip: principle and applications," Sensors and Actuators, 1-8, 1998.
Stipp, D., "Gene Chip Breakthrough," at http://linkage.rockefeller.edu/wli/news/affymetrx.html (last visited Jul. 23, 1997).
Gasson, S., "Maskless fabrication of light-directed oligonucleotide microarrays using a digital micromirror array," Nature Biotechnology, 17: 974-978, 1999.
Volkan et al., "A New Surface-Enhanced Raman Scattering Substrate Based on Silver Nanoparticles in Sol-Gel," 30: 1057-1065, 1999.
Vo-Dinh et al., "Surface-enhanced Raman Scattering (SERS) Method and instrumentation for Genomics and Biomedical Analysis," J. Raman Spectrosc. 30: 785-793, 1999.

* cited by examiner

*Primary Examiner*—Gary Benzion
*Assistant Examiner*—Heather Calamita
(74) *Attorney, Agent, or Firm*—Akerman Senterfitt; Eduardo J. Quiñones

(57) ABSTRACT

A Raman integrated sensor system for the detection of targets including biotargets includes at least one sampling platform, at least one receptor probe disposed on the sampling platform, and an integrated circuit detector system communicably connected to the receptor. The sampling platform is preferably a Raman active surface-enhanced scattering (SERS) platform, wherein the Raman sensor is a SERS sensor. The receptors can include at least one protein receptor and at least one nucleic acid receptor.

22 Claims, 21 Drawing Sheets

A)

B)

Double-Stranded DNA

Hybridization Principle

Various methods for immunosensing. (A) Competitive assay, (B) direct assay, and (C) sandwich assay

SERS DIAGNOSTIC PLATFORMS, METHODS AND SYSTEMS MICROARRAYS, BIOSENSORS AND BIOCHIPS

CROSS-REFERENCE TO RELATED APPLICATIONS

This application is a Continuation-In-Part of application Ser. No. 09/771,530 filed on Jan. 29, 2001 now U.S. Pat. No. 6,448,064, entitled INTEGRATED CIRCUIT BIOCHIP, which is a Continuation of application Ser. No. 08/979,672 entitled INTEGRATED CIRCUIT BIOCHIP MICROSYSTEM CONTAINING LENS filed on Nov. 26, 1997 and issued as U.S. Pat. No. 6,197,503 B1 on Mar. 6, 2001, and is also a Continuation-in-Part of application Ser. No. 09/890,047 filed on Jul. 25, 2001 entitled ADVANCED MULTI-FUNCTIONAL/MULTISPECTRAL BIOSENSOR DEVICES AND METHODS OF USE, which is a Continuation-In-Part of application Ser. No. 09/236,758 filed Jan. 25, 1999 entitled ADVANCED MULTIFUNCTIONAL BIOCHIP AND METHODS OF USE.

STATEMENT REGARDING FEDERALLY SPONSORED RESEARCH OR DEVELOPMENT

The United States Government has rights in this invention pursuant to Contract No. DE-AC05-00OR22725 between the United States Department of Energy and UT-Battelle, LLC.

FIELD OF THE INVENTION

The invention relates to sensors including biosensors and methods for molecular identification, particularly SERS platforms and systems and methods for molecular identification based on Raman and surface-enhanced Raman scattering (SERS).

BACKGROUND OF THE INVENTION

There is a demand for a rapid, simple, cost-effective technique for screening air, water and blood samples to identify various components therein. Screening can involve detection of harmful chemicals, bacteria and viruses. For example, there is a need for early medical diagnostics, genomics assays, proteomics analyses, drug discovery screening, and detection of biological and chemical warfare agents for homeland security and defense.

Screening can also be used to identify the presence or absence of medical diseases and infectious pathogens. Regarding blood, the use of inexpensive screening analyses can allow the rapid detection and improved treatments of many illnesses. Rapid and effective medical screening tests can also reduce the cost of health care by preventing unnecessary and costly reactive medical treatment.

A critical factor in many diagnostics is the rapid, selective, and sensitive detection of biochemical substances, such as proteins, metabolites, nucleic acids, biological species or living systems, such as bacteria, virus or related components at ultra-trace levels in samples provided. In the case of medical diagnostic applications, biological samples can include tissues, blood and other bodily fluids. To achieve the required level of sensitivity and specificity in detection, it is often necessary to use a biosensor that is capable of identifying and differentiating between a large number of biochemical constituents in complex samples.

Living systems possess exquisite recognition elements, such as antibodies, enzymes and genes, often referred to as bioreceptors, which allow specific identification and detection of complex chemical and biological species. Biosensors exploit this powerful molecular recognition capability of bioreceptors. Due to the high level of specificity of the DNA hybridization process, there is an increasing interest in the development of DNA bioreceptor-based analytical systems. Applications for these systems include infectious disease identification, medical diagnostics and therapy, biotechnology and environmental bioremediation.

There has been recent research and development relating to biosensors. One type of biosensor device, often referred to as a "biochip," applies spectroscopy using a semiconductor-based detection system and biotechnology-based probes. Bioprobes have been receiving increasing interest as of late. These probes have generally included luminescence labels, such as fluorescent or chemiluminescent labels for gene detection. Although sensitivities achieved by luminescence techniques are generally adequate for certain applications, alternative techniques with improved spectral selectivities are desirable to overcome the limited spectral specificity generally provided by luminescent labels.

Spectroscopy is an analytical technique concerned with the measurement of the interaction of radiant energy with matter and with the interpretation of the interaction both at the fundamental level and for practical analysis. Interpretation of the spectra produced by various spectroscopic instrumentation has been used to provide fundamental information on atomic and molecular energy levels, the distribution of species within those levels, the nature of processes involving change from one level to another, molecular geometries, chemical bonding, and interaction of molecules in solution. Comparisons of spectra have provided a basis for the determination of qualitative chemical composition and chemical structure, and for quantitative chemical analysis.

Vibrational spectroscopy is a useful technique for characterizing molecules and for determining their chemical structure. The vibrational spectrum of a molecule, based on the molecular structure of that molecule, is a series of sharp lines which constitutes a unique fingerprint of that specific molecular structure. If the vibrational spectrum is to be measured by an optical absorption process, optical fibers from a source is delivered to a sample, and after passage through the sample, an optical signal generated by the exciting optical energy is collected. This collected light is directed to a monochromator equipped with a photodetector for analyzing its wavelength and/or intensity.

One particular spectroscopic technique, known as Raman spectroscopy, utilizes the Raman effect, which is a phenomenon observed in the scattering of light as it passes through a material medium, whereby the light experiences a change in frequency and a random alteration in phase. When light is scattered from a molecule, most photons are elastically scattered. The scattered photons have the same energy (frequency) and, therefore, wavelength, as the incident photons. However, a small fraction of light (approximately 1 in $10^7$ photons) is scattered at optical frequencies different from, and usually lower than, the frequency of the incident photons. The process leading to this inelastic scatter is termed the Raman effect. Raman scattering can occur with a change in vibrational, rotational or electronic energy of a molecule.

The difference in energy between the incident photon and the Raman scattered photon is equal to the energy of a vibration of the scattering molecule. A plot of intensity of scattered light versus energy difference is a Raman spectrum. The wavelengths present in the scattered optical energy are characteristic of the structure of the molecule, and the intensity of this optical energy is dependent on the concentration of these molecules.

Numerically, the energy difference between the initial and final vibrational levels, v, or Raman shift in wavenumbers ($cm^{-1}$), is calculated through equation 1 below:

$$v = (1/\lambda_{incident}) - (1/\lambda_{scattered}) \quad (1)$$

Where $\lambda_{incident}$ and $\lambda_{scattered}$ are wavelengths (in cm) of the incident and Raman scattered photons, respectively. The vibrational energy is ultimately dissipated as heat. Because of the low intensity of Raman scattering, heat dissipation does not cause a measurable temperature rise in the material.

Raman spectroscopy is complementary to fluorescence, and has been used as an analytical tool for certain applications due to its excellent specificity for chemical group identification. However, low sensitivity historically has limited its applications.

Recently, the Raman technique has been rejuvenated following the discovery of a Raman enhancement of up to $10^6$ to $10^{10}$ for molecules adsorbed on microstructures of metal surfaces. The technique associated with this phenomenon is known as surface-enhanced Raman scattering (SERS) spectroscopy. The enhancement is due to a microstructured metal surface scattering process which increases the intrinsically weak normal Raman scattering (NRS) due to a combination of several electromagnetic and chemical effects between the molecule adsorbed on the metal surface and the metal surface itself.

The enhancement is primarily due to plasmon excitation at the metal surface. Thus, the effect is generally limited to Cu, Ag and Au, and to a few other metals for which surface plasmons are excited by visible radiation. Although chemisorption is not essential, when it does occur there may be further enhancement of the Raman signal, since the formation of new chemical bonds and the consequent perturbation of adsorbate electronic energy levels can lead to a surface-induced resonance effect. The combination of surface- and resonance-enhancement (SERS) can occur when adsorbates have intense electronic absorption bands in the same spectral region as the metal surface plasmon resonance, yielding an overall enhancement as large as $10^{10}$ to $10^{12}$.

Raman spectroscopy has become an important analytical technique for chemical and biological analysis due to the wealth of information on molecular structures, surface processes, and interface reactions that can be extracted from experimental data. The Raman technique has been used with gene probe biosensors. U.S. Pat. No. 5,814,516 ('516 patent) to the same Inventor as the instant invention entitled "Surface enhanced Raman gene probe and methods thereof" discloses a gene probe biosensor comprising a support means, a SERS gene probe having at least one oligonucleotide strand having at least one SERS label, and a SERS active substrate disposed on the support means. The support means has at least one SERS gene probe adsorbed thereon. Biotargets such as bacterial and viral DNA, RNA and PNA are detected using a SERS gene probe via hybridization to oligonucleotide strands complementary to the SERS gene probe. The '516 patent does not disclose or suggest operatively connecting a Raman gene probe with an integrated circuit detection system to produce a biochip capable of SERS detection.

SUMMARY OF THE INVENTION

This invention describes Raman and SERS assay methods and systems including microarrays, biosensors and biochips for the detection of biotargets such as DNA, proteins and pathogens using receptor probes. Receptor probes may include one or more bioreceptors selected from antibodies, DNA, enzymes, tissues, organelles, as well as other receptor probes, and combinations thereof.

An integrated Raman sensor system for the detection of targets including biotargets includes at least one sampling platform. A plurality of receptor probes are disposed on the sampling platform. The receptor probes are adapted for binding with at least one target molecule. The receptor probes generate a Raman signal when combined with the target molecule responsive to electromagnetic radiation applied to the target, the receptor, or both the receptor and target. Application of electromagnetic radiation to the target, the receptor, or to both the receptor and target following the binding of at least one target to the receptor is hereafter referred to as electromagnetic radiation applied to the "receptor/target combination." An integrated circuit based detection system detects the Raman signal from the receptor/target combination. The sampling platform can be a surface-enhanced Raman scattering (SERS) platform.

The integrated circuit based detector system can include a plurality of detection channels for detection of Raman signals relating to any of the plurality of receptor probes. At least one of the plurality of detection channels can be dedicated to each of the plurality of receptor probes.

The receptor probes can be selected from DNA, RNA, antibodies, proteins, enzymes, cells or cell components, and biomimetics. Biomimetics can be molecular imprint antibodies, DNA-based aptamers, peptide nucleic acid (PNA), cyclodextrins and dendrimers.

The sampling platform can be physically separated from the detection system. Alternatively, the sampling platform can be disposed on the detection system, such as in contact with the same.

The system can further include a microfluidic system having a plurality of microfluidic channels, the microfluidic system for directing samples through the microfluidic channels to the plurality of receptor probes. The microfluidic system can be a capillary electrophoresis array, a liquid chromatography array, a gas chromatography array, or a lab-on-a-chip system.

The sampling platform can comprise a tape. In this embodiment, the system can include a structure for translating the tape, such as a reel-to-reel.

The target and/or the plurality of receptor probes can include at least one SERS label. Alternatively, SERS labels can be unbound if provided in proximity to the receptor probes and/or target molecules. The SERS labels can include cresyl fast violet, cresyl blue violet, rhodamine-6G, para-aminobenzoic acid, phthalic acids, erythrosin or aminoacridine.

The sampling platform can include metal nanoparticle islands, metal coated nanospheres, metal coated alumina, metal coated titanium dioxide, metal coated silica, metal coated membranes or metal membranes.

The system can include at least one excitation source of electromagnetic radiation for generating the Raman signal upon application of electromagnetic radiation to the receptor/target combination. The excitation source can be a low pressure lamp, a light emitting diode, a diode array, a laser and a laser array. The excitation source can be disposed either on-chip or off-chip.

The integrated circuit detection system can include at least one photodetector. Photodetectors can be selected from photodiodes, avalanche photodiodes, phototransistors, photomultipliers, CCDs, CIDs and hybrid photomultipliers. The detection system can also include a signal amplification system or a signal processing system, the signal amplification system or signal processing system preferably disposed on-chip. The on-chip signal amplification system or signal processing system can include a microprocessor or an amplifier. In another embodiment of the invention, A SERS sensor system for the detection of targets includes at least one randomly-addressable SERS (RASERS) platform. The RASERS platform includes a microelectrode array having a plurality of array elements, the array elements each capable of being independently biased. A plurality of receptor probes are disposed on the sampling platform, the receptor probes generating a Raman signal when combined with a target molecule responsive to electromagnetic radiation applied to the receptor/target combination.

An external detection system or an integrated circuit based detection system can be communicably connected to the receptors/target for detection of the Raman signals. The system can include a control system for controlling bias provided to the plurality of array elements.

A Raman sensor system for the simultaneous detection of a plurality of diverse targets including biotargets includes at least one sampling platform and a plurality of receptors disposed on the sampling platform. The plurality of receptors include at least one protein receptor and at least one nucleic acid receptor. The receptor probes generate a Raman signal when combined with a target molecule in response to electromagnetic radiation applied to the receptor/target combination. A detection system is communicably connected to the receptors/targets, the detection system adapted for detection of the Raman signals. The sensor system can be a SERS sensor system.

A sensor system for the simultaneous detection of a plurality of diverse targets including biotargets includes at least one sampling platform. The sampling platform includes a plurality of receptors, the plurality of receptors including at least two different receptor types, the receptor types selected from the group consisting of a protein receptor, a nucleic acid receptor, a cellular or cellular component detector, and a biomimetic detector. The receptors generate a Raman signal when combined with the target molecule responsive to electromagnetic radiation applied to the receptor/target combination. A detection system is communicably connected to the receptors and is adapted for detection of Raman signals.

A method for the SERS detection of targets including biotargets includes the steps of providing a surface-enhanced Raman scattering (SERS) integrated sensor system having at least one surface-enhanced Raman scattering (SERS) active sampling platform, wherein at least one receptor is disposed on the sampling platform, and an integrated circuit detector system for detecting a Raman signal generated when the target molecule is combined with the receptor to form a receptor/target combination is radiated with electromagnetic radiation. A sample suspected of containing at least one target is introduced to the receptor. The receptor/target combination is then radiated with electromagnetic radiation. Raman radiation scattered by the receptor/target combination is then analyzed. The analyzing step can comprise gene mapping, gene identification, DNA sequencing, medical diagnostics, drug discovery screening, and environmental bioremediation.

A method for the detection of targets including biotargets using surface-enhanced Raman scattering (SERS) includes the steps of providing a SERS-active sampling platform, wherein a plurality of receptors are disposed on the sampling platform. The plurality of receptors include at least one protein receptor and at least one nucleic acid receptor, or at least two receptor types selected from the group of types consisting of a protein receptor, a nucleic acid receptor, a cellular or cellular component receptor, and a biomimetic receptor. When present, the receptor/target generates a Raman signal upon irradiation with electromagnetic radiation. A sample suspected of containing at least one target is introduced to the receptor. The receptor (if unbound with the target) or the receptor/target combination (if the target is bound to the receptor) is then radiated. Raman radiation resulting from the radiating step is then analyzed.

A method for forming a SERS-active surface platform including a plurality of SERS-active receptor sites includes the steps of providing a gel or polymer material having metallic precursor particles embedded therein. The gel or polymer material is then radiated with light, wherein a plurality of SERS nanoparticles are photogenerated.

The light can be directed through a photomask, the photomask having a plurality of regions transparent to the light. Alternatively, the light can be directed through a diffractive optical filter, the diffractive optical filter for splitting the light into a plurality of light beams. As a further alternative, the light can be directed to a digital microarray mirror, the digital microarray mirror splitting the light into a plurality of light beams. The method can include the step of disposing a plurality of receptor probes on the SERS-active platform.

A method for forming a SERS-active surface platform including a plurality of SERS-active receptor sites includes the steps of providing a solid support material, coating a plurality of nanospheres onto the solid support. A layer of SERS-active metal is deposited on the nanosphere coated solid support, the SERS-active metal for providing conduction electrons required for generation of surface plasmons.

BRIEF DESCRIPTION OF THE DRAWINGS

A fuller understanding of the present invention and the features and benefits thereof will be accomplished upon review of the following detailed description together with the accompanying drawings, in which.

DETAILED DESCRIPTION OF THE PREFERRED EMBODIMENTS

A Raman system and method are disclosed which allows simultaneous detection of a wide variety of desired target molecules, including biotargets and chemical targets using Raman or Surface-Enhanced Raman Scattering (SERS) detection techniques. SERS is generally preferred to standard Raman spectroscopy since it provides significantly improved signal levels. Accordingly, the invention will generally be described in terms of a SERS system and method. However, the invention can be used with non-surface-enhanced Raman scattering, although accommodation will generally be required in the form of increased excitation source power. The invention can be used for a broad range of applications, such as development of low-cost diagnostic biochips for medical applications, homeland security, environmental monitoring and high-throughput screening.

In a preferred embodiment of the invention, the sampling platform is a SERS platform, permitting the system to be SERS sensor. The SERS sampling platform includes one or more structured metal surfaces. A plurality of receptor probes are disposed anywhere within the range of the enhanced local field emanating from the structured metal surfaces. The Raman enhancement occurs upon irradiation of the structured metal surfaces. Such receptor probe proximity permits SERS enhancement of the Raman signal from the receptor probe/target combination which is formed following a binding event, such as hybridization in the case of DNA. As used herein, a receptor is referred to as being "disposed on" a structured metal surface when it is either adsorbed thereon or within the range of the enhanced local field generated by the structured metal surface upon irradiation, such as within a few tens of angstroms.

The receptor probes are preferably bioreceptor probes. The bioprobes are bound to the SERS active surface, collectively referred to as a SERS-active sampling platform. Bioprobes can be disposed on metal surfaces or metal surfaces can be disposed both above and below the bioprobes.

A detection system is communicably connected to the receptors. In one embodiment, the detection system is an integrated circuit based detection system capable of receiving and processing optical signals.

Biosensors and biochips involve two essential functions that integrate "biological recognition" and "sensing." The basic principle of an optical biosensor is to detect molecular recognition and to transform it into an optical signal using a transducer. The biochip is a biosensor which involves the combination of integrated circuit elements, an electrooptic excitation/detection system, and one or more receptor probes, generally referred to as bioprobes, into a self-contained and integrated microdevice. The detection system is preferably a multi-channel system. For example, when a plurality of receptor probes are used, one dedicated detection channel can be provided to receive signals emanating from each of the plurality of receptor probes.

Figure 1:
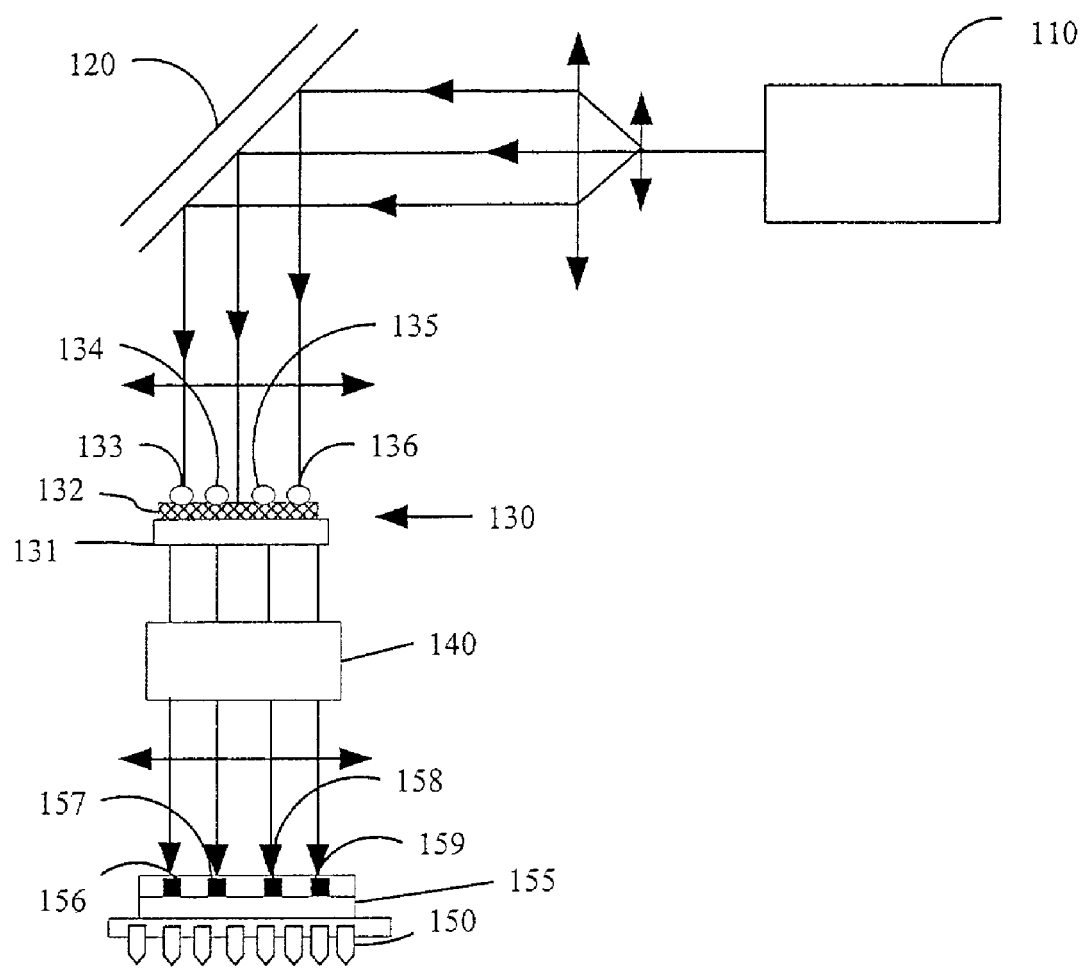
FIG. 1 shows a diagram of an exemplary SERS biochip device, according to an embodiment of the invention.

FIG. 1 shows a schematic diagram of an exemplary SERS biochip device 100, according to an embodiment of the invention. Excitation source 110 provides excitation source energy in the form of substantially monochromatic light. The excitation light source 110 can be disposed on-chip or off-chip. For example, the excitation light source can be a laser or a light emitting diode (LED), or an array of these sources.

Mirror 120 directs incident light to SERS-active platform 130. SERS active platform 130 includes substrate 131, a plurality of structured metal surfaces 132 and a plurality of receptor probes 133-136 disposed on the structured metal surfaces 132.

Receptor probes 133-136 can include at least one SERS active label. The target analyte can also include a SERS active label. Both the receptor probes 133-136 and target analyte can both include SERS active labels. As a further alternative, both the receptor probes 133-136 and the target analyte can both be provided without a SERS active label. In this embodiment, a detectable SERS shift occurs following a binding event. In yet another alternate embodiment, floating SERS active labels may be provided in proximity to receptor probes 133-136, where for example, the SERS label material may intercalate with receptor probes 133-136 or the target analyte.

Excitation source energy can be directed by mirror 120 towards the surface of platform 130 or along the edge of platform 130. In the case the excitation source energy is incident along the edge of platform 130, platform 130 can act as a waveguide and absorb energy emitted from the excitation source and convert the energy received into an evanescent wave which can be supported within the waveguide material provided by platform 130.

Optical filter system 140 transmits Raman signals from the receptor probes which may be bound to target molecules onto the sampling platform 130, but rejects scattered photons having the same energy as the incident photons. With Raman, as with other detection modes such as fluorescence and phosphorescence detection modes, the Rayleigh scattered light can be kept separate from the emitted Raman light using appropriate optical filters to block the Rayleigh scattered light from reaching the detection system. The optical filter system 140 can include a holographic notch filter and wavelength selection filter.

Microchip 150 includes Raman sensing platform 155. Sensing platform 155 includes detection elements 156-159, such as phototransducers, which receive Raman signals inelastically scattered by the receptor probes 133-136 which may be bound to target molecules, and converts the same to an electrical signal, such as a current signal. Sensing platform 155 can use integrated circuit based electrooptic sensing photodetectors, such as photodiodes, phototransistors, avalanche diodes and CCDs. Highly integrated biosensors are made possible partly through the capability of fabricating multiple optical sensing elements and microelectronics on a single integrated circuit (IC). An example of such integration is a two-dimensional array of optical detector-amplifiers integrated on a single IC chip.

In a preferred biochip embodiment, the invention uses either integrated phototransistor detector array or integrated photodiode detector array based detection systems. The biochips can include a large-area, n-well integrated amplifier-photodiode array that has been designed as a single, custom integrated circuit (IC), fabricated for the biochip. For example, photodiode detector array based detection systems having 100 channels (10×10 array) have been built.

The IC device is coupled to the multi-array sampling platform and is designed for monitoring very low light levels, such as $10^{-12}$ amperes, or less. The individual photodiodes fabricated have 900 µm square size and are arrayed on a 1-mm spacing grid. The photodiodes and the accompanying electronic circuitry were fabricated using a standard 1.2-micron n-well CMOS process, although, current embodiments can make use of reduced feature size processes, such as 0.13 µm processes, or below. The use of this type of standard process allows the production of photodiodes and phototransistors as well as other numerous types of analog and digital circuitry on a single IC chip.

This feature is the main advantage of the CMOS technology in comparison to other detector technologies such as charge-coupled devices (CCD) or charge-injection devices. The photodiodes themselves are produced using the n-well structure that is generally used to make resistors or as the body material for transistors. Since the anode of the diode is the p-type substrate material, which is common to every circuit on the IC chip, only the cathode is available for monitoring the photocurrent and the photodiode is constrained to operate with a reverse bias.

The microchip 150 is an integrated circuit which preferably provides a plurality of detection channels. Each channel may include one or more signal processing devices. However, a separate detection system may be used as an alternative to the integrated microchip detector shown in FIG. 1. Signal processing devices can include a transimpedance amplifier (e.g. operational amplifier) for converting the current signal output by the photodector elements to a voltage signal. Signal processors can also include one or more amplifiers (e.g. operational amplifier) for amplifying the signal, and one or more filters, such as low-pass or band-pass filters. The microchip 150 can also provide analog-to-digital (A/D) converters. If each of a plurality of detection channels are provided an input to the A/D converter, a fully parallel readout of all of the detection channels can be obtained. Data from the microchip 150 can be supplied to a suitable computing system for data analysis.

Figure 2:
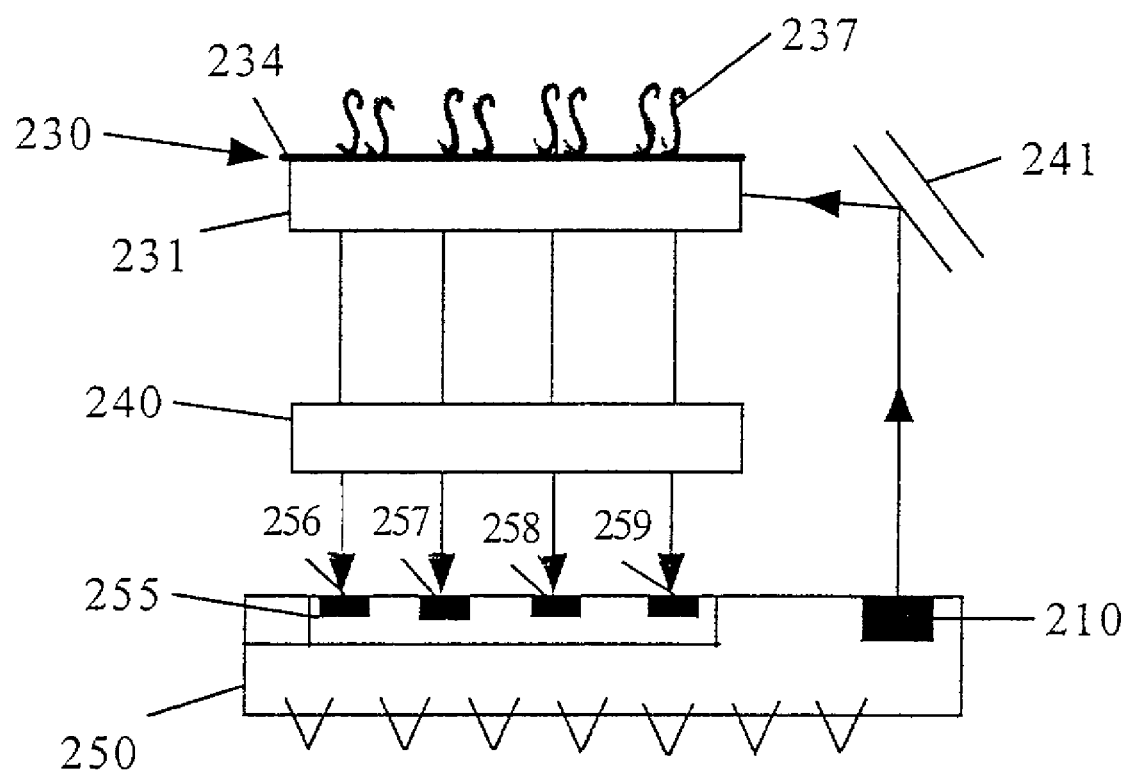
FIG. 2 shows a diagram of an exemplary SERS biochip device having an on-chip light source and a removable sampling platform, according to an embodiment of the invention.

The sampling platform can be integrated with the biochip or disposed in a spaced apart relation. FIG. 2 shows a SERS biochip system 200 which includes an on-chip excitation light source 210 and a removable SERS based sampling platform 230 disposed in a spaced apart relation with microchip 250. On-chip light source 210 can be a laser, such as a laser diode.

SERS sampling platform 230 includes substrate 231, SERS active surface 234 and a plurality of receptor probes, such as bioprobes 237, disposed on the SERS active surface 234. Optical filter system 240, and microchip 250 having Raman sensing platform 255 including detection elements 256-259 disposed thereon are also included with biochip system 200.

Mirror 241 can direct light from on-chip radiation source 210 to desired locations on sampling platform 230. FIG. 2 shows mirror 241 directing light to the side of sampling platform 230 so that the light falls within the acceptance angle of substrate 231, the acceptance angle being half the vertex angle of that cone within which optical power may be coupled into bound modes of the optical fiber provided by substrate 231. Mirror 241 may also be a MEMS mirror (not shown), the MEMS mirror being disposed on microchip 250.

Sampling platform 230 can be mechanically supported by a suitable mechanical support structure (not shown). For example, the supporting structure can be in the form of discrete columns or a continuous hollow structure originating on microchip 250 and terminating along the periphery of sampling platform 230. Periphery contact of the support structure can limit the interference caused by the supporting structure on the transmission of electromagnetic energy to detection elements 256-259 on microchip 250.

This configuration provides certain advantages. For example, this configuration allows removal of the sampling platform 230, such as for cleaning or replacing the platform. The system can have removable disposable SERS sampling platform substrates. The removable SERS platform 230 can be disposed of after use.

Figure 3:
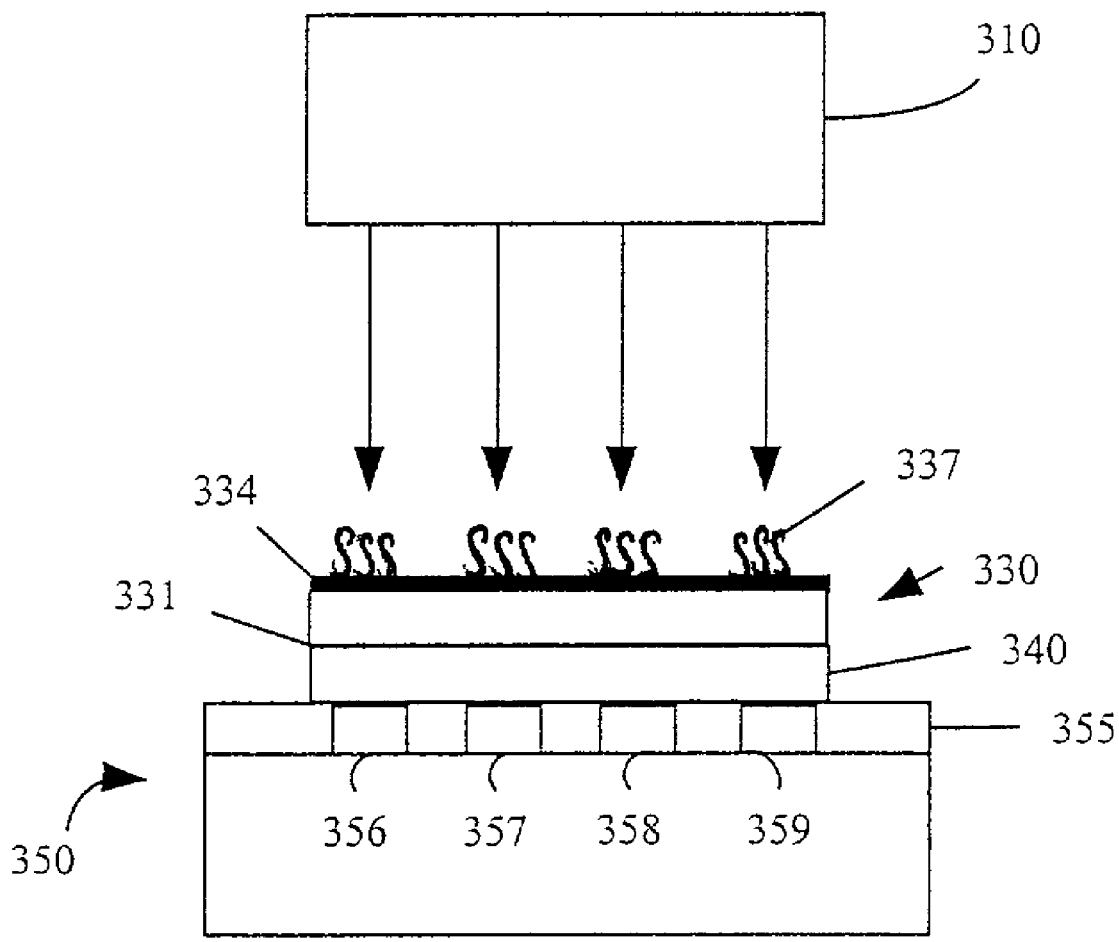
FIG. 3 shows a diagram of an exemplary SERS biochip device having an integrated sampling platform, according to another embodiment of the invention.

A SERS biochip 300 having an integrated sampling platform configuration is shown in FIG. 3 along with external excitation source 310. In this configuration, SERS based sampling platform 330 is disposed on microchip 350. SERS sampling platform 330 includes substrate 331, SERS active surface 334 and a plurality of bioprobes 337 disposed on the SERS active surface 334. Substrate 331 of SERS-active sampling platform 330 is disposed on an optical filter system 340, the optical filter system 340 being disposed on the surface of microchip 350. Microchip 350 includes Raman sensing platform 355, sensing platform 355 including detection elements 356-359.

This configuration can provide improved optical coupling between the SERS sampling platform 330 the microchip 350 with its associated sensing platform 355. In this configuration, the entire chip can be removed or cleaned after each measurement, as opposed to the disposable SERS sampling platform shown in FIG. 2. With CMOS manufacturing technology, entire chips can be produced at very low cost and thus can be made to be disposable items.

A separate non-integrated detection system can be used with the invention. With conventional imaging, the optical emission from every pixel of an image can be recorded but only at a specific wavelength or spectral bandpass. With conventional spectroscopy, the signal at every wavelength within a spectral range can be recorded, but for only a single analyte spot.

When multiple Raman labels are used for detection of a plurality of targets, a preferred detection system includes multi-spectral sensors (MSS) capable recording SERS signals across the entire (2-D) sampling platform area. Since the various receptor probe locations will generally emit distinct Raman signals even if a single label or tag is used, a detector capable of multi-spectral sensing is generally required for this purpose.

Bioprobes can include antibody, DNA, proteins including enzymes, cells or cell components, and biometric probes. Biometric probes can include molecular imprint antibodies, DNA-based aptamers, and peptide nucleic acids (PNA). These bioprobes can be mixed and matched on a common sampling platform. Thus, the biochip can be a multifunctional diagnostic device, capable of detecting, for example, both DNA and antigens, or DNA and proteins, simultaneously. In one preferred embodiment, the sampling platform includes at least one protein receptor and at least one nucleic acid receptor.

Bioprobes and/or targets can include one or more SERS labels or tags attached thereto. Alternatively, tags can be disposed in proximity to the bioprobes and/or targets, but as free molecules not being in contact with the same. Tags can emit a detectable or altered signal when the bioprobe is combined with its intended target, such as a nucleic acid target. The tagged or labeled species may emit Raman energy.

Different SERS labels can be used for different target bioprobes, such as oligonucleotide strands of different sequences and different bacterial and viral types. Examples of SERS labels that can generally be used include cresyl fast violet (CFV), cresyl blue violet, brilliant cresyl blue (BCB), rhodamine-6G, para-aminobenzoic acid, phthalic acids, erythrosin, as well as aminoacridine.

Other SERS labels that can be used that are inert to hybridization or binding in general. Useful SERS labels include chemical elements or structures that may exhibit a characteristic Raman or SERS emission.

With respect to DNA probes, a SERS label can be attached at the end of the oligonucleotide strand or it can be disposed within the oligonucleotide strand. More than one SERS label can be used on a given oligonucleotide strand. As noted earlier, the SERS label can be attached or disposed with either the probe oligonucleotide strand or the target oligonucleotide strand.

Again described with respect to DNA probes, another embodiment is one in which two oligonucleotide strands are used for the SERS gene probe and the SERS label is disposed intercalated between the probe oligonucleotide strand and the target oligonucleotide strand. This particular embodiment provides the label to be held in place by the two strands. In this configuration, there is no attachment of the label on the oligonucleotide strands. More than one SERS label may be used for this embodiment as well.

The SERS label can be designed such that its Raman characteristics (e.g., intensity, frequency, polarization) change depending upon whether a single oligonucleotide strand is labeled with the SERS label or whether a hybridized double oligonucleotide strand is labeled with the SERS label, or whether the SERS label is in an unbound free state. When using such a label, it is not necessary to bind the label to an oligonucleotide strand, but the SERS label may be delivered as a free molecule. If hybridization occurs, these specially designed SERS labels can be intercalated or entrapped in the double strand (e.g. intercalated). If hybridization does not occur, then the SERS label remains in a free state.

Figure 4:
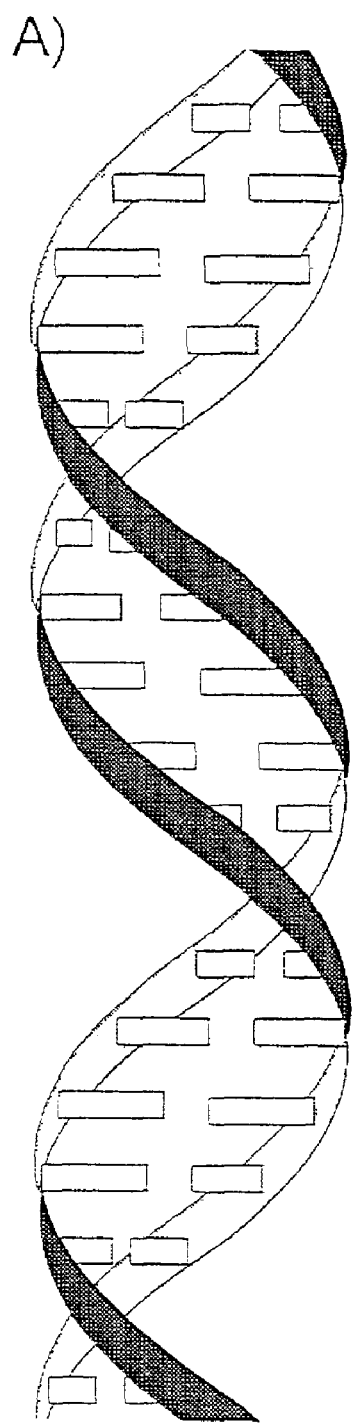
FIG. 4 shows hybridization involving the joining of a single strand of a nucleic acid with a complementary probe sequence.
Figure 4:
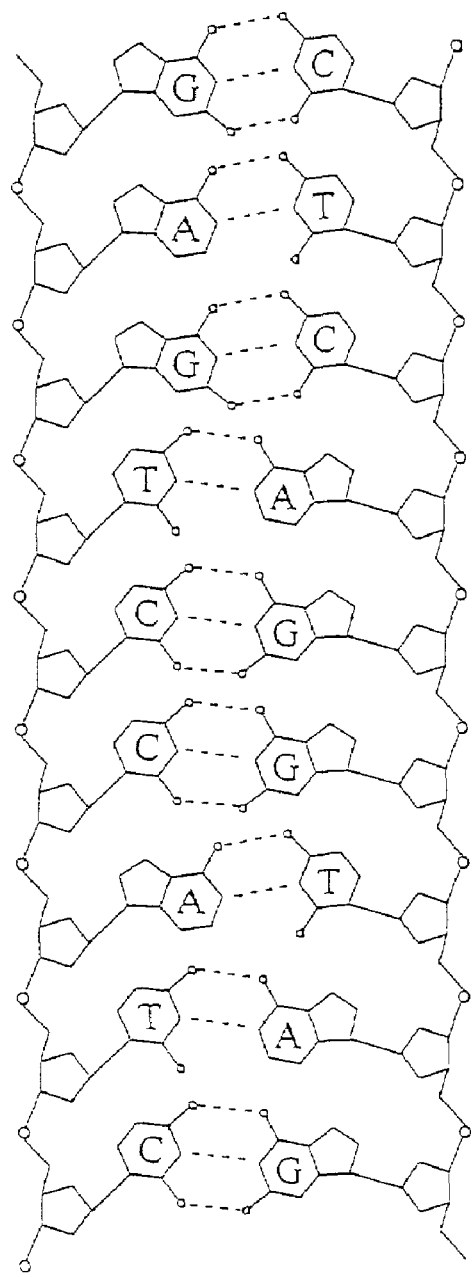

The operation of DNA (gene) probes is based on the hybridization process, while the operation of an antibody probe is through a more general binding process that does not involve hybridization. Hybridization involves the joining of a single strand of nucleic acid with a complementary probe sequence as shown in FIG. 4. Hybridization of a nucleic acid probe to a DNA biotarget, such as a gene sequence, bacteria and viral DNA offers a very high degree of accuracy for identifying DNA sequences complementary to that of the probe. Nucleic acids strands tend to be paired to their complements in the corresponding double-stranded structure. Therefore, a single-stranded DNA molecule will seek out its complement in a complex mixture of DNA containing large numbers of other nucleic acid molecules. Hence, a nucleic acid probe, such as a gene probe, provides a detection method which can be very specific to DNA sequences. Factors affecting the hybridization or reassociation of two complementary DNA strands include temperature, contact time, salt concentration, the degree of mismatch between the base pairs, and the length and concentration of the target and probe sequences.

The SERS method can also be used to monitor gene expression and RNA using cDNA probes. Genes, which are housed in the DNA of the cell's nucleus, contain codes that are recipes for tens of thousands of proteins. The code-containing regions of the gene (exons), however, are often separated by much noncoding DNA (introns). A cDNA molecule is a laboratory-made version of a gene that contains only its code-containing information-rich regions. These molecules provide a way for genome researchers to focus on regions in the genome that represent biologically important regions.

Antibody probes may also be used with the invention, preferably with other receptor probe types, such as DNA probes, on a common sampling platform. Antibodies are the product of immune system cells (B cells) when those cells are exposed to antigenic substances or molecules. The antibodies produced following antigen exposure have recognition/binding sites for specific molecular structures (or substructures) of the antigen. Just as specific configurations of a unique key enable it to enter a specific lock, so in an analogous manner, an antigen-specific antibody "fits" its unique antigen. Thus, an antigen-specific antibody interacts with its unique antigen in a highly specific manner, so that the total three-dimensional biochemical conformation of antigen and antibody are complementary. This molecular recognition feature of antibodies is the key to their usefulness in immunosensors; molecular structural recognition allows one to develop antibodies that can bind specifically to chemicals, biomolecules and microorganism components.

Such antibodies may then be used as specific "probes" to identify an analyte of interest that is often present in extremely small amounts, among a myriad of other chemical substances. Another property of antibodies of great importance to their role in immunosensors is the strength or avidity/affinity of the antigen-antibody interaction. Since the antigen-antibody surfaces lie in close proximity to one another, a variety of molecular interactions may take place and the overall strength of such interactions can be considerable, with correspondingly highly favorable association and equilibrium constants.

Figure 5:
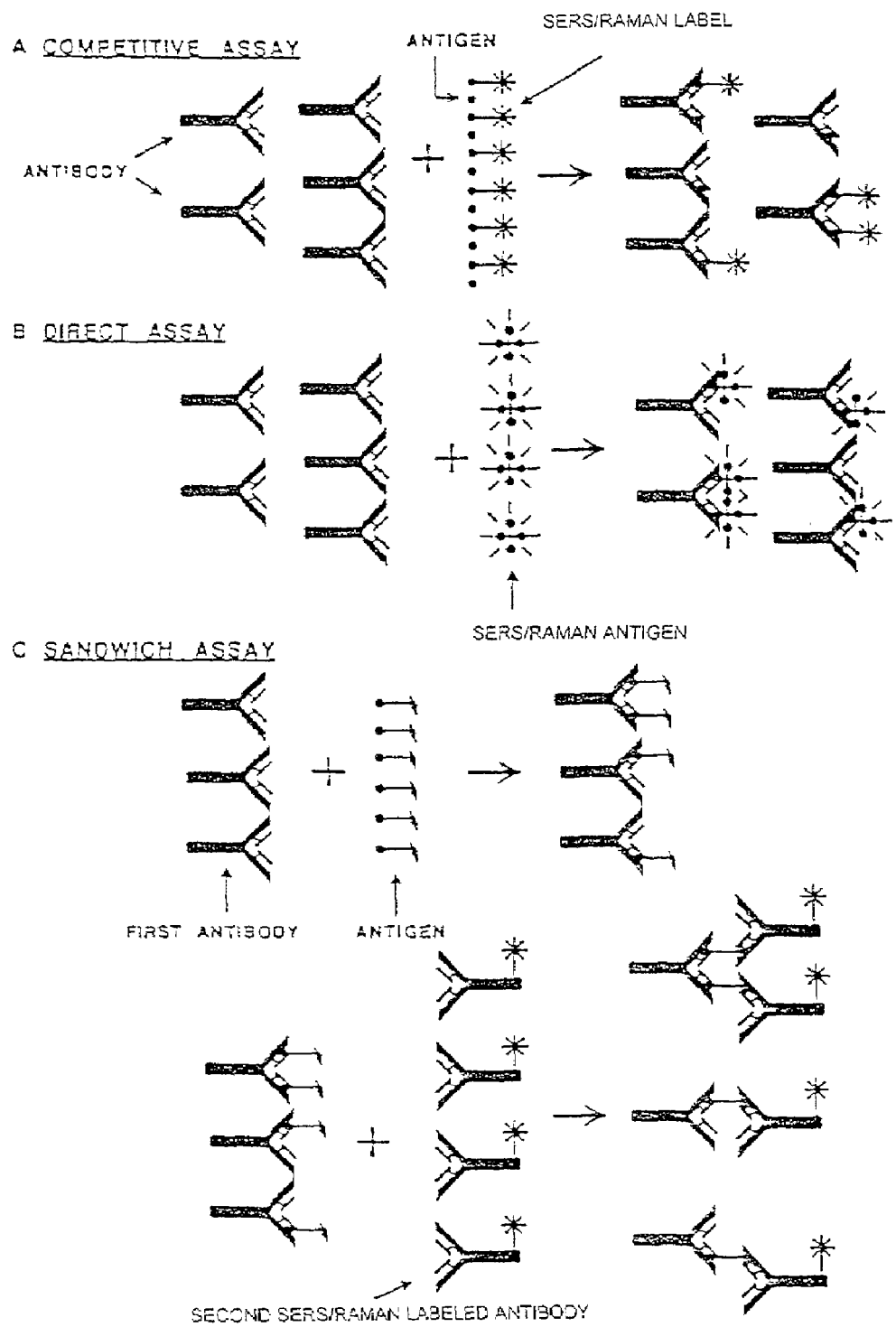
FIG. 5 shows three assaying methods for immunsensing using SERS/Raman labels.

SERS based immunoassay measurement strategies can be divided into three categories: competitive, direct and sandwich assays. FIG. 5(A)-(C) show schematics of the three different possible strategies. Assays can be performed in a SERS active medium, such as in solution using sol-gel or on a SERS active solid or gel substrate. Labels can be fluorescent labels, Raman or SERS active molecules, although FIGS. 5(A)-(C) will be described relative to SERS active labels.

In competitive assays (FIG. 5(A)), a SERS labeled antigen is used to compete with an unlabeled antigen for a limited number of antibody binding sites. Antibody-bound antigen (labeled and unlabeled) is separated from free antigen and the SERS signal of the antibody-bound labeled antigen is measured. The signal intensity of the bound phase is inversely proportional to the concentration of the unlabeled antigen.

Direct assays (FIG. 5(B)) are performed by simply incubating the antigens with excess amounts of antigens. The sensitivity is directly proportional to the amount of antibody present and the response is directly proportional to the amount of antigen present. The higher the SERS signal, the lower the unlabeled antigen concentration.

Sandwich assays (FIG. 5(C)) are performed by incubating the antigens with a primary (first) antibody which is present in excess concentrations. The antibody-antigen complex is then incubated with a second SERS labeled antibody which binds to the first antibody. Unbound labeled antibody is rinsed away and the bound labeled antibody is measured. Sensitivity is related to the amount of primary antibodies present with the response proportional to the antigen concentration.

Other types of bioreceptors that can be used in the SERS or Raman biochip system. For example, proteins including enzymes, cells or cell components and biomimetic probes such as "molecular imprint" antibodies, DNA-based aptamers, peptides nucleic acids (PNA), cyclodextrins and dendrimers may be used with the invention. Such probes are bound onto SERS platforms as described in detail later in the application.

SERS Sampling Platform

A useful component in the SERS system is the SERS-active sampling platform. The role of this sampling platform is to enhance the Raman signal emitted by the receptor probes or associated labels following detection of the target by the receptor probes.

Immobilization of bioprobes on the SERS-active sampling platform can be to a transducer detection surface to ensure optimal contact and maximum detection. When immobilized onto a substrate, the bioprobes are stabilized and, therefore, can be reused repetitively. In the simplest procedure, hybridization is performed on an immobilized target or a probe molecule attached on a SERS-active solid surface described below.

Figure 6:
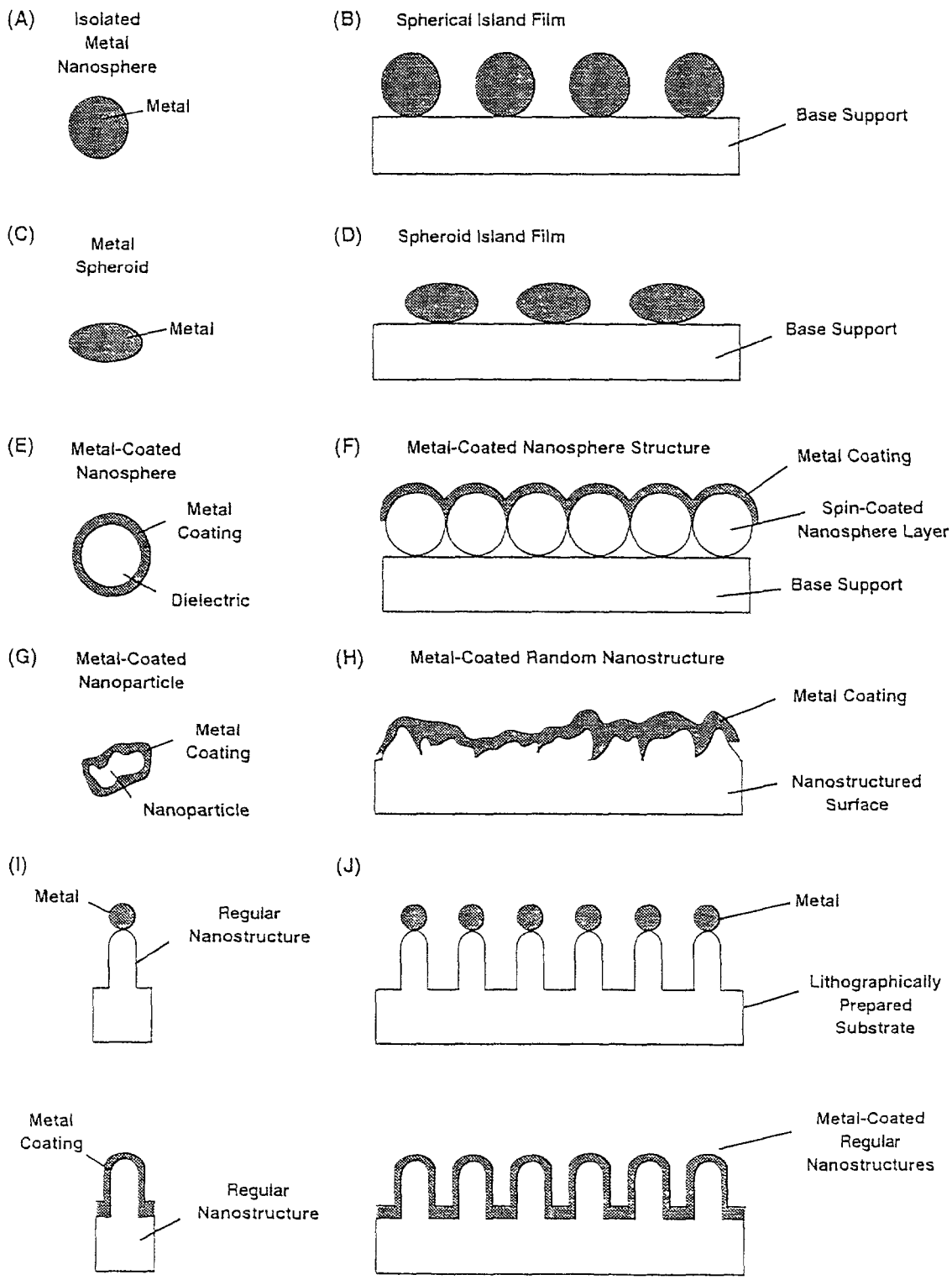
FIG. 6 shows several SERS sampling platform structures.

FIG. 6 shows some exemplary SERS-active sampling platforms suitable for use with SERS systems, including SERS biochips. A simple structure is shown in FIG. 6(A) as an isolated metal nanosphere particle and in FIG. 6(B) where a plurality of these particles are integrated onto a base support material. Similarly, FIGS. 6(C) and (D), respectively, show metal spheroid and a plurality of these particles integrated onto a base support material. FIGS. 6(E) and (F), respectively, show metal coated dielectric nanospheres and a plurality of these particles integrated onto a base support material. FIGS. 6(G) and (H), respectively, show metal coated dielectric nanoparticle and a plurality of these particles integrated onto a base support material, wherein the nanoparticles have random nanostructures. FIGS. 6(I) and (J), respectively, show metal spheres disposed on a regular nanostructure. The regular nanostructure is preferably prepared using lithographic techniques. Similarly, FIGS. 6(K) and (L), respectively, show a metal coated regular nanostructure and a plurality of these structures integrated onto a base support material.

Alternatively, a metallic nanostructure platform can be produced by evaporating a thin layer, generally being less than 10 nm thickness, of a metal such as silver, gold or other suitable metals onto a solid base support such as a sampling platform. Under these conditions, the silver or gold layer forms nanoparticles on the support in the form of isolated metal islands. Upon any significant increase of the deposited metal thickness, the particles generally start to coalesce and form a continuous film. Absent significant surface roughness, a continuous film is generally undesirable as it will generally limit the SERS enhancement effect.

The size and shape of the metal nanoparticles can be influenced by varying the thickness of metal deposited as measured by a quartz crystal monitor perpendicular to the evaporation source. Another alternative method involves sputter-deposited thin films of metals as SERS-active substrates.

SERS platforms can be based on silver, gold or other suitable metal coated nanosphere substrates as shown in FIGS. 6(E) and (F). One of the earlier difficulties in the development of the SERS technique for analytical applications had been the production of surfaces or media that had an easily controlled protrusion size (roughness) and reproducible structures. An approach involves the use of nanospheres coated on a solid support, such as by spin-coating, in order to produce and control the desired roughness. The nanostructured support is subsequently covered with a layer of silver, gold or other suitable metals that provide the conduction electrons required for the surface plasmon mechanisms.

Among the techniques based on solid substrates, the methods using simple nanomaterials, such as polytetrafluoroethylene (Teflon) or latex nanospheres, appear to be the simplest to prepare. Teflon and latex spheres are commercially available in a wide variety of sizes. The shapes of these materials are very regular and their size can be selected for optimal enhancement. The effect of the sphere size and metal layer thickness upon the SERS effect can be easily investigated.

Results have indicated that, for each sphere size, there is an optimum silver layer thickness for which the maximum SERS signal is observed. Silver-coated nanospheres are known to be among the most strongly enhancing substrates investigated, with enhancement factors comparable to or greater than those found for electrochemically roughened surfaces.

Preparation of the nanosphere coated substrates can involve delivery of a 50-μL volume of a suspension of latex or Teflon nanospheres onto the surface of the substrate. Different types of potentially useful substrates include filter paper, cellulosic membranes, glass plates, and quartz materials. The substrate can then be placed on a high-speed spinning device and spun at 800 to 2000 rpm for about 20 s. The spheres adhere to the glass surface, providing uniform coverage. The silver (gold or other metals) is then deposited on the nanosphere-coated substrate in a vacuum evaporator at a deposition rate of 0.15-0.2 nm/s. The thickness of the silver (gold or other metals) layer deposited is generally 50 to 100 nm.

SERS platforms can be based on metal-coated alumina nanoparticles, such as shown in FIGS. 6(E) and 6(G) where alumina is the dielectric core of the nanoparticles. SERS studies have shown that nanoparticles with irregular shapes (FIG. 6(G)) can be used instead of regularly shaped nanospheres to spin-coat solid substrates. For instance, alumina appears to be one of the most efficient materials for the production of SERS-active substrates. One important advantage of alumina over Teflon or latex nanospheres is its very low cost. The preparation of the substrate can be a method similar to techniques used to form fumed silica.

The alumina surface consists of randomly distributed surface agglomerates and protrusions in the 10 to 100 nm range. These structures produce large electromagnetic fields on the surface when the incident photon energy is in resonance with the localized surface plasmons. Alumina-based substrates, due to their efficiency, low cost and simplicity for preparation, have led to a wide variety of practical applications.

SERS platforms can be based on metal coated titanium dioxide nanoparticles, where titanium dioxide is the dielectric core of the nanoparticles. For example, silver, gold and or other SERS active metals and their alloys may be used. Titanium dioxide is an alternate material that can be used to produce the nanostructure roughness when coated on surfaces. The procedures to prepare these substrates is similar to that used for nanospheres using alumina particles. Titanium dioxide materials are first deposited on glass and cellulose substrates and then coated with a 50 to 100 nm layer of silver, gold or other metals by thermal evaporation as described previously. Prior to deposition, titanium dioxide is prepared as a suspension in water (e.g., 10% concentration by weight). The silver-coated titanium oxide surfaces obtained by this method can provide efficient SERS-active substrates.

SERS platforms can be based on metal-coated silica nanoparticles, where silica is the dielectric core of the nanoparticles. Another type of substrate that is quite SERS active and relatively simple to prepare is a fumed silica-based substrate. Fumed silica has been used as a thickening agent in various industrial processes, including coating and cosmetics preparations. In the preparation of SERS materials, the selection of the appropriate types of fumed silica is important. Fumed silica is manufactured in different grades, which vary with respect to surface area, particle diameter, and degree of compression. The fumed silica particles are suspended in a 10% water solution and coated onto a glass plate or filter paper. The substrate is then coated with a 50 to 100 nm layer of silver, gold or other metals using techniques including thermal evaporation. With this type of substrate, the fumed silica material, which has nano-sized structures, provides the rough-surface effect for the SERS process.

SERS platforms can be based on lithographic and grating structures on SERS-active surfaces. Lithographic techniques have been used to produce controlled surface roughness. These surfaces consist of uniform arrays of isolated silver (gold or other metals) nanoparticles which are uniform in shape and size. These surfaces produce a Raman enhancement on the order of $10^7$ and have been used to test the electromagnetic model of SERS.

SERS platforms can be based on etched quartz substrates. It is sometimes difficult to produce periodic structures over large areas using lithographic techniques. A procedure using etched quartz posts avoids this difficulty by using an island film as an etch mask on a $SiO_2$ substrate. The preparation of $SiO_2$ prolate posts is a multi-step operation that involves plasma etching of $SiO_2$ with a silver island film as an etch mask. Since fused quartz is etched much more slowly than is thermally deposited quartz, a 500 nm layer of $SiO_2$ is first thermally evaporated onto fused quartz at a rate of about 0.1 to 0.2 nm/s. The resulting crystalline quartz is annealed to the fused quartz for 45 min. at approximately 950° C. A 5 nm silver (gold or other metals) layer is then evaporated onto the thermal $SiO_2$ layer and the substrate is flash-heated for 20 s at 500° C. This heating causes the thin silver (gold or other metals) layer to bead up into small globules, which act as etch masks.

The substrate is then etched for 30 to 60 min. in a $CHF_3$ plasma to produce submicron prolate $SiO_2$ posts, which are then coated with a continuous 80-nm silver layer at normal evaporation angle. Another method consists of varying the angle of evaporation in order to produce silver nanoparticles on the tips of the quartz posts. Raman enhancement for several polyaromatic molecules adsorbed on etched quartz substrates has been investigated and showed a 10-fold enhancement compared to island films and cross-grating structures.

SERS platforms can be based on metal-coated cellulose or membranes. Direct metal coating of special filter papers or membranes, such as Nylon, or materials used in biological assays coated with silver, gold or other metals, can provide useful substrates. Certain types of micropore filter papers coated with a thin layer of evaporated silver, gold or other metals appear to provide efficient SERS-active substrates. Scanning electron micrographs of these cellulosic materials showed that these surfaces consist of fibrous 10 μm strands with numerous tendrils that provide the necessary protrusions required for the SERS enhancement.

SERS platforms can be based on metal membranes. One of the simplest types of solid substrates is a silver or gold membrane used for air particulate sampling. The filter already has micropores and interstices that provide the roughness features required to induce SERS. These substrates consist of silver, gold or other metals membranes and can therefore be used directly as SERS-active substrates without requiring silver coating.

SERS platforms can also be based on chemically, electrochemically etched metal and other roughened surfaces. Chemical etching procedures can also be used to produce SERS-active metal surfaces. In one procedure, copper foil is etched for 40 min. in 2 mol. $dm^{-3}$ nitric acid at room temperature. Another procedure consists of sandblasting copper foil with $Al_2O_3$ at 4 bar pressure and subsequently etching for 2 min. SEM pictures of the metal surfaces indicate that both etching procedures can produce surface roughness on the 10 to 100 nm scale. The etched copper surfaces have been used to investigate the SERS emission of a polycyclic aromatic dye, Nile Blue. The resonance Raman signals of Nile Blue were enhanced by 103 to 104 relative to the molecule in solution. This enhancement was only a factor of 2 smaller than the corresponding value for a silver-particle surface. Electrochemically roughened silver oxide substrates have been developed to detect the vapor of chemical nerve agent stimulants. (Taranenko et al, Jnl of Raman Spectroscopy, Vol. 30, 379, 1996).

SERS platforms and other patterned metal structures can be based on metal nanoparticles embedded in sol gels. For example, the below described method can be used to form a variety of electrically conductive structures, such as electrically conductive lines disposed on a substrate material (e.g. Si), the lines having area dimensions based on the dimension of the optical beam, without the need for masking. The optical beam may also be scanned if desired.

In the case of SERS platforms, the sampling platforms using SERS-active sol gel materials preformed in desired sampling devices. A surface-enhanced Raman scattering (SERS)-active silver chloride silica/glass substrate was prepared by using an in-situ precipitation of silver chloride particles in sol-gel films as a precursor for nanoparticles of silver (Ref: M. Volkan, D. L. Stokes and T. Vo-Dinh, J. Raman Spectroscopy, 30, 1057, 1999). The controlled precipitation of silver chloride was achieved by the reaction of silver nitrate with trichloroacetic acid which leads to a slow release of chloride ions. Silver chloride particles were reduced to silver nanoparticles by $FeSO_4.7H_2O$.

Figure 20:
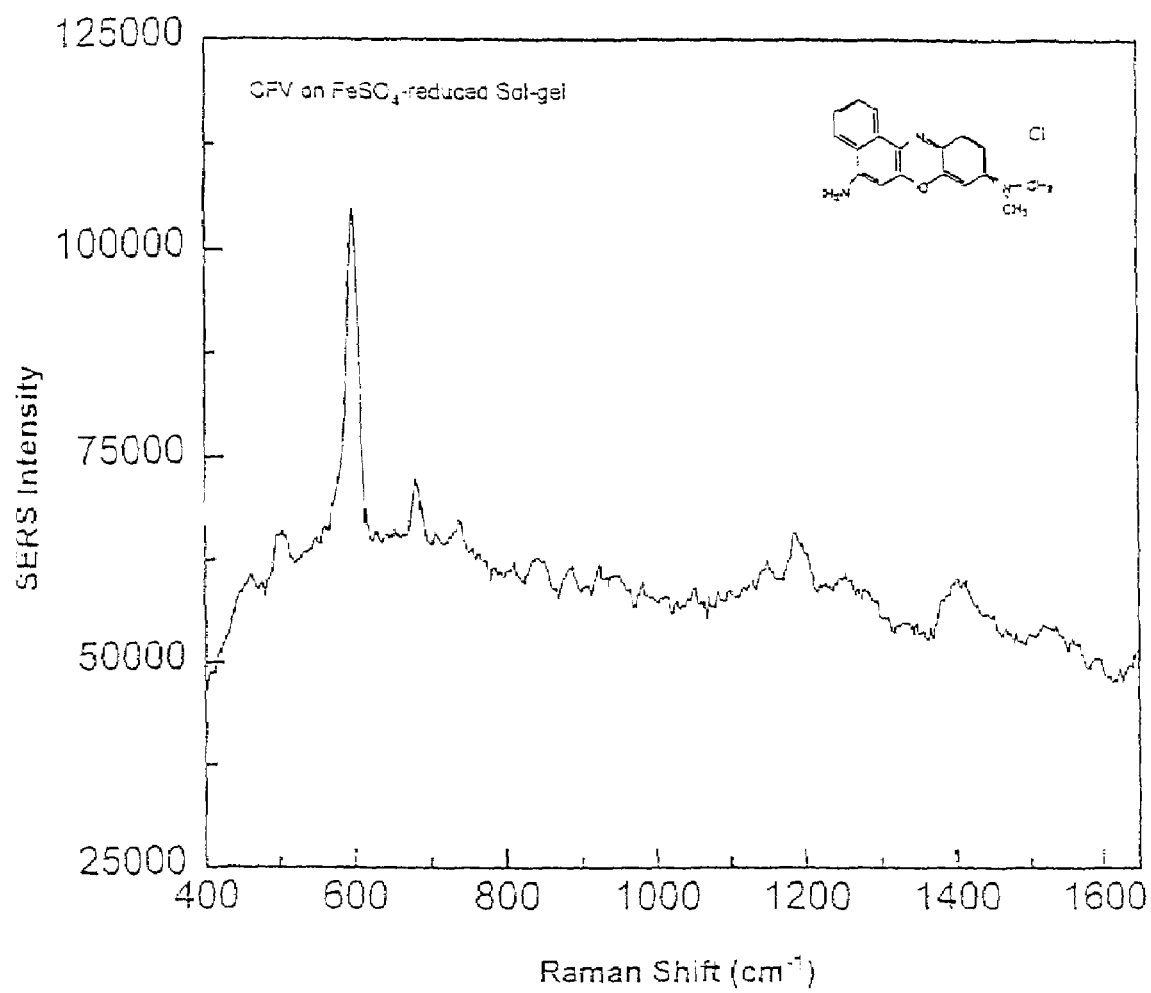
FIG. 20 shows a SERS spectrum from a sol gel substrate using crystal fast violet (CFV) dye as a DNA label.

The sol-gel films prepared exhibit good optical properties and induce a strong SERS effect for several model compounds, including cresyl fast violet (CFV) and brilliant cresyl blue (BCB). Precursor sols were prepared by hydrolysis of TEOS (Tetra ethyl orthosilane) and MTEOS (methyltriethoxysilane) in water/ethanol solution, using $HNO_3$ as a catalyst. $AgNO_3$ (silver nitrate) and $CCl_3CO_2H$ [trichloroacetic acid (TCAA)] were added in various ratios. The final coating solution had the following composition: 1.3 mL TEOS, 1.3 mL MTEOS, 5.3 mL ethanol, 0.8 mL of water, 1.3 mL ethylene glycol (EG), 1.5 mL 3-M $AgNO_3$, 0.5 mL 3-M TCAA (Ag:Cl,1:1), and 0.03 mL concentrated $HNO_3$. FIG. 20 shows the effectiveness of this sol gel substrate for the crystal fast violet (CFV) dye that has been used as the DNA label in certain studies.

SERS platforms can be based on metal nanoparticles embedded in a polymer. A SERS-active polymer substrate can include a polyvinyl alcohol (PVA) matrix that is embedded with isolated silver nanoparticles (T. Vo-Dinh, D. L. Stokes, G. D. Griffin, M. Volkan, U. J. Kim and M. L. Simpson, Journal Raman Spectroscopy, 30, 785, 1999). The silver nanoparticles are reduced from silver nitrate mixed within the PVA matrix. There are several advantages to this type of substrate. Perhaps the most significant advantage is its accessibility. The preparation does not require the use of an expensive vacuum evaporation system for fabrication and is relatively simple and inexpensive. The polymer support matrix provides suitable durability for practical field application. The PVA-based substrates can be prepared in the following manner: 0.045 g of $AgNO_3$ was added to 1.56 g of 10% (w/w) aqueous solution of PVA. The mixture is then stirred at room temperature for 24 h. The resulting solution can be spin-coated on glass plates (prepared from microscope slides as described above). The coated plates can be subsequently dried in an oven at 100° C. for 1 h. Prior to SERS measurements, dried substrates can be finally dipped into $FeSO_4.7H_2O$ (4% w/w) solution and again dried in an oven at 100° C. for 15 min.

Figure 7:
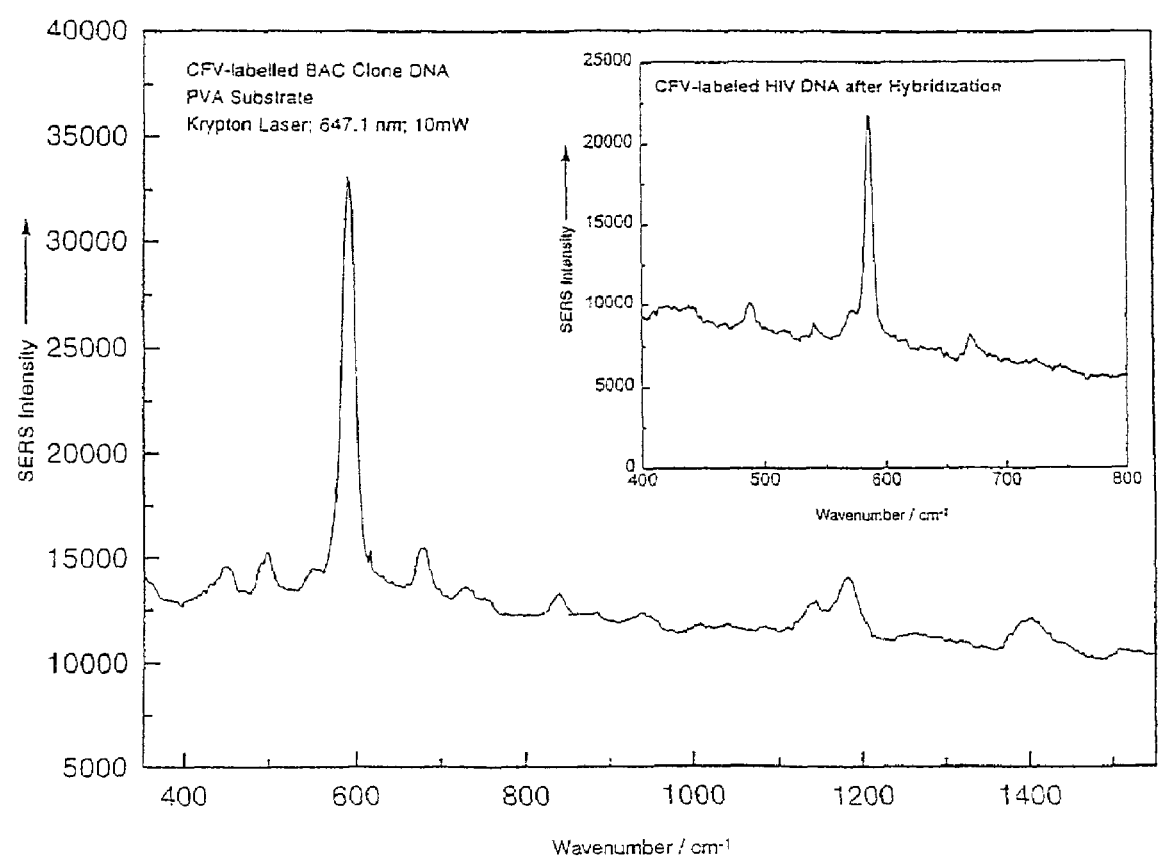
FIG. 7 shows the detection of a BAC clone DNA labeled with CFV using a SERS platform.

FIG. 7 shows the detection of a BAC clone DNA labeled with CFV using the PVA SERS platform. The inset provided shows positive hybridization of a CFV labeled probe bound to its target HIV gene.

SERS platforms can be a patterned SERS platform. In this configuration, the SERS-active areas form an array pattern. The bioreceptors can then be directly attached to the SERS-active patterned arrays. Various methods to prepare the SERS arrays are described in the following sections.

Figure 8:
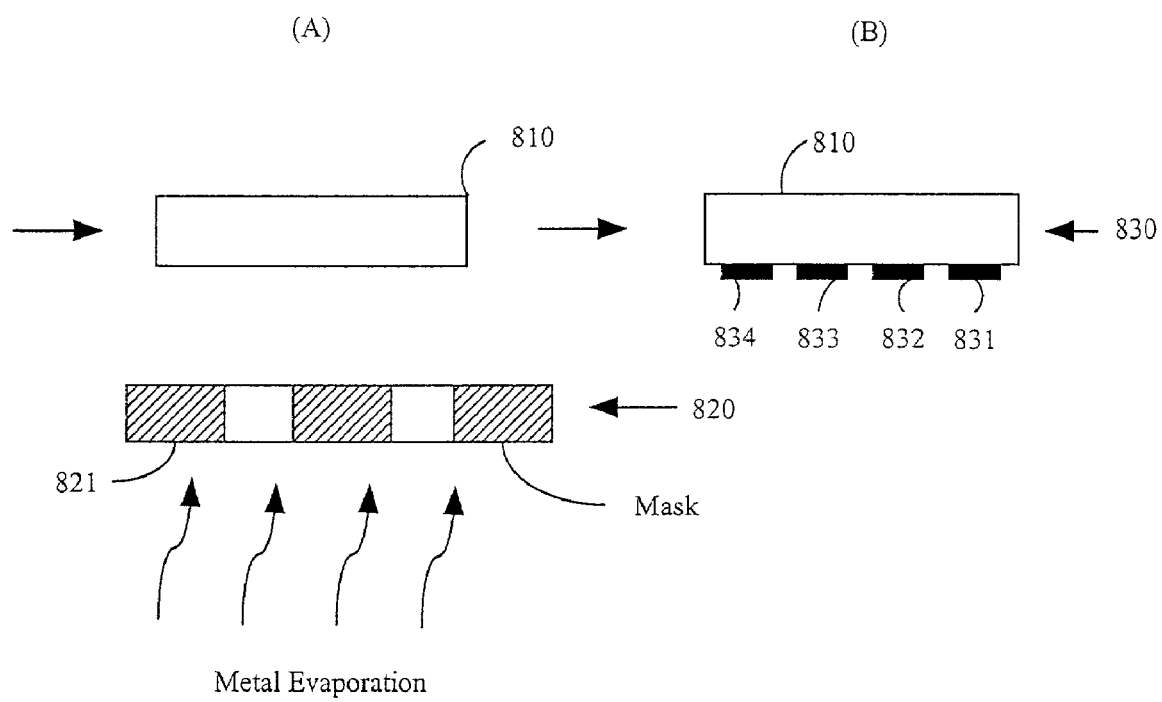
FIGS. 8(A) and (B) show steps in the formation of a SERS active array using evaporation and a physical mask.

Metal evaporation using physical masks can be used to prepare a SERS active patterned array as shown in FIGS. 8(A) and (B). The masks can be contact or non-contact masks.

The array can be fabricated by evaporating a suitable metal, such as silver, onto a substrate 810 through a physical mask 820 having an array of holes 821 that allow the metal to evaporate through the mask. In one example embodiment, the hole 821 spacing can be 1 mm center-to-center, with the hole openings each being 800 μm. FIG. 8(B) shows a pattern of SERS active sites 831-834, each site 831-834 corresponding to the holes 821 in physical mask 820. SERS active sites 831-834 disposed on substrate 810 comprise SERS active array pattern 830.

Alternatively, a simple SERS active metallic nanostructure can be produced by evaporating a thin layer (preferably less than 10 nm thickness) of a metal such as silver directly onto a solid base support. Under these conditions the silver layer forms nanoparticles on the support in the form of isolated metal islands. Upon an increase of the deposited silver thickness, the particles would start to coalesce and form a continuous film. The size and shape of the metal nanoparticles can be influenced by varying the thickness of metal deposited (as measured by a quartz crystal monitor perpendicular to the evaporation source). Metal can be evaporated onto both disposable substrates (see FIG. 2) or directly on the microchip detection area of the integrated microchip platform (see FIG. 3).

Figure 9:
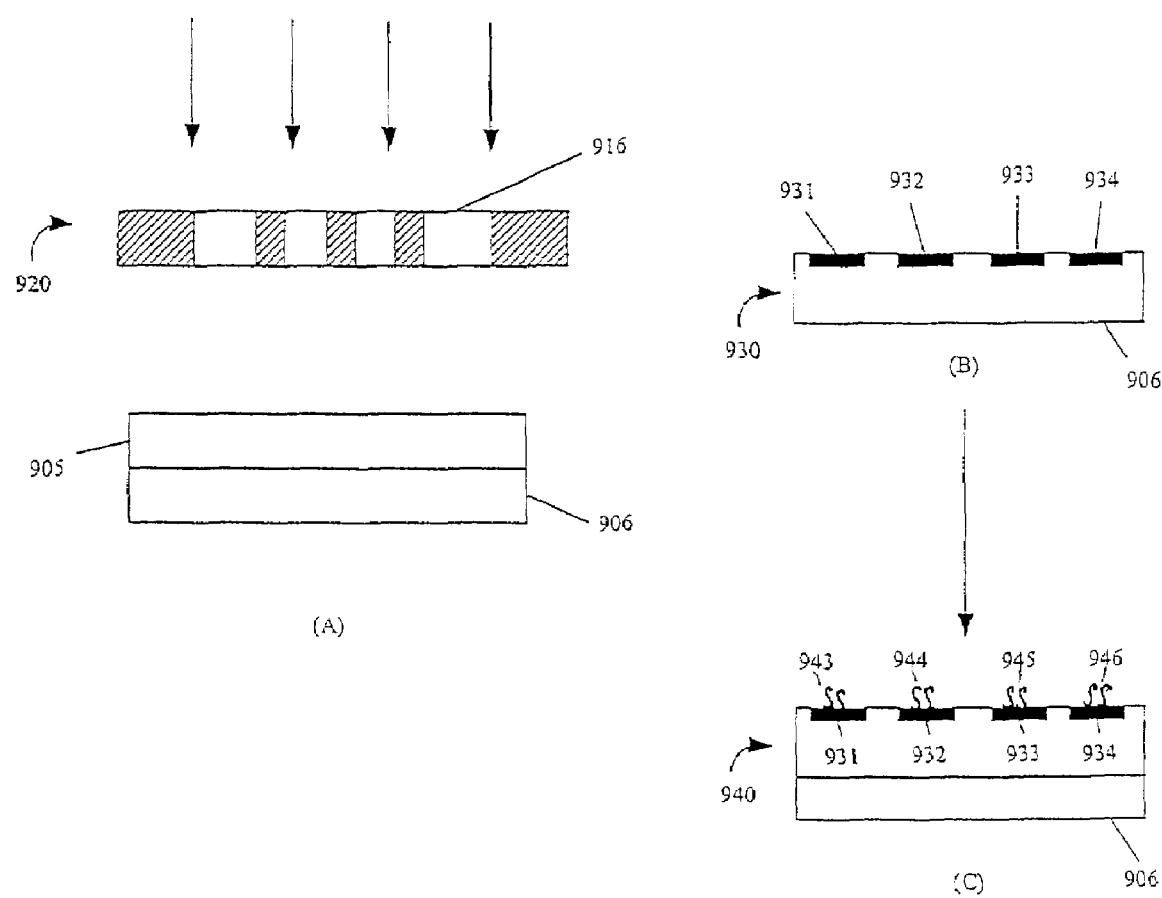
FIGS. 9(A)-(C) show steps in the formation of SERS platforms using an optical mask.

SERS active platforms can also be fabricated using optical masks as shown in FIGS. 9(A)-(C). Using this technique, SERS nanoparticles as well as metal layers can be photogenerated. FIG. 9(A) shows a gel or polymeric material 905 disposed on a support 906. Gel or polymeric material includes liquid phase metal precursor molecules. Light 910, such as 350 nm light, is directed towards photomask 920, the photomask having a plurality of regions 916 which are substantially transparent to light 910. The thickness of the gel or polymeric material generally determines the intensity used in this method. Light, as use herein refers to electromagnetic radiation, in general, and is not limited to the visible light spectrum.

Light causes reduction of precursor molecules, such as AgCl into Ag nanoparticles, the Ag nanoparticles forming SERS active medium 930 including SERS active sites 931-934 as shown in FIG. 9(B). FIG. 9(C) shows a SERS active sampling platform 940 including a plurality of bioprobes 943-946 which are disposed on the photogenerated SERS active sites 931-934.

Instead of using an optical mask diffractive optical filter that form microarray spots from a light beam can be used. A maskless technique using digital micromirror array probes to illuminate the platform with microarray of light can also be used (Singh-Gasson S, Green R D, Yue Y, Nelson C, Blattner F, Sussman R, Cerrina F, Nature Biotechnology 10 974-978 (1999)).

SERS platforms can be formed by patterning bioprobes on a continuous SERS platform. If the SERS-active surface is continuous, a pattern of bioprobes is generally required.

Figure 10:
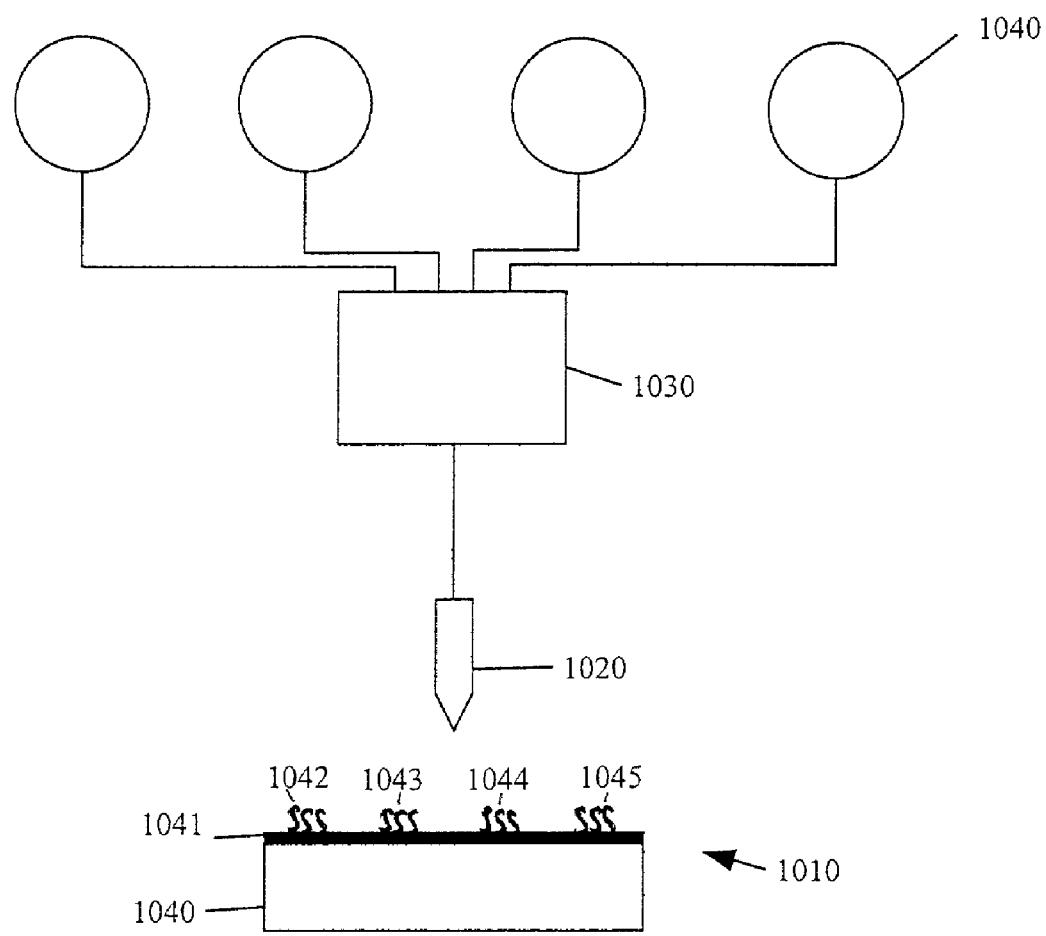
FIG. 10 shows a method for dispensing bioprobes or reagents to form an array pattern of bioprobes on a SERS sampling platform.

FIG. 10 illustrates a system 1000 and method for dispensing probe material on a sampling platform 1010 using a microfluidics system. Reagent reservoir 1040 supplies fluid material (e.g. solutions of DNA) to microfluidic system 1030 for transfer of the fluid to a fluid dispensing device 1020. Fluid dispensing device 1020 can include a micropipette, microject or microbubble spotting device, each device including one or more small diameter glass capillaries, dispensing device 1020 preferably held a few millimeters above sampling platform as shown in FIG. 10.

Microjet or microbubble technology is commonly used in inkjet printing devices. Fluid is dispensed by dispensing device 1020 on substrate 1040, the surface of substrate 1040 coated with SERS active metal layer 1041 to form an array of bioprobes 1042-1045. Dispensing device 1020 can also be a pneumatic Picopump, such as produced by World Precision Instruments, Sarasota, Fla. Picopumps are capable of producing consistent microspots with diameter size ranges of 500-800 μm, which can be selected to match the area of the biochip detector elements (not shown).

Colloidal solutions of metals such as silver can produce nanoparticles that may be used to enhance the Raman signal. Silver colloid hydrosols are often used to produce SERS-active media in solutions. In this embodiment, hybridization or binding can first be performed on a solid platform by exposure of receptor probes to a suitable target containing sample. The platform can be covered by a silver or a gold nanoparticle solution. This procedure could be easily implemented with current hybridization schemes. Silver colloids are generally prepared by rapidly mixing a solution of $AgNO_3$ with ice-cold $NaBH_4$. Gold and silver colloids have been investigated as SERS-active media for various dyes.

A procedure implementing the PVA additive can be used to produce silver sol solutions that are still active several months after preparation. The sols used can be prepared by methods outlined previously. The sols can be made with sodium citrate and silver nitrate or sodium borohydride and silver nitrate. The methods are quite different because of the differences in the reducing potential of the two reductants. The borohydride is added batchwise over an hour to an ice-cold solution of silver nitrate with PVA added during the process to a final concentration of 1%. The final solution is boiled for one hour to destroy any remaining borohydride. These sols are generally stable for several months.

Immobilizing Bioprobes on the SERS Sampling Platform

Receptor probes can be bound onto surfaces, such as a SERS patterned platform, in a number of ways. For example, for biologically active DNA, antibody and other receptor probe materials can be directly or indirectly immobilized onto a SERS-active area of the transducer detection surface to ensure optimal contact and maximum detection. When immobilized onto a platform, the probes are stabilized and, therefore, can be reused repetitively.

Regarding gene probes, in one of the simplest procedures, hybridization is performed on an immobilized target or a probe molecule attached to a solid surface such as a nitrocellulose, a nylon membrane or a glass plate. Several methods can be used to bind probes, such as DNA, to different metal or non-metal supports. The method commonly used for binding DNA to gold involves thiol chemistry which involves S—Au bonding.

Another approach involves binding DNA onto glass (or polymer materials) and then activating (SERS activation) these surfaces by coating them with metal nanoparticles. For example, silanization methods have been used to bind to glass surfaces using 3-glycidoxypropyltrimethoxysilane (GOP) or aminopropyltrimethoxysilane (APTS) and to covalently link DNA via amino linkers incorporated either at the 3' or 5' end of the molecule during DNA synthesis.

Another approach consists of immobilizing the gene probe onto a SERS-active membrane and subsequently attaching the membrane to the transducer detection surface. This approach avoids the need of binding the bioreceptor onto the transducer and could possibly allow easier large-scale production. Several types of membranes are available for DNA binding: nitrocellulose, charge-modified nylon, etc. The gene probe can then be bound to the membrane using ultraviolet activation.

For a DNA probe, the first step in membrane hybridization is immobilization of single-stranded target nucleic acids to the selected surface of the probe, such as a membrane, waveguide or optical fiber. The probes are then treated with hybridization buffer to block nonspecific nucleic acid binding sites. The probe is introduced to samples containing labeled DNA and allowed to hybridize by reestablishing a double-stranded molecule with the complementary target sequences. After hybridization, excess unbound labeled probe is washed off, and the hybrid target sequences detected.

Arrays of DNA probes can be produced on the sampling platform by spotting the DNA on appropriate membrane/ platforms using a pV 830 pneumatic Picopump (World Precision Instruments, Sarasota, Fla).

Agglomerate-free alumina (0.1-mm nominal particle diameter) which can be used to prepare the SERS platforms can be obtained from Baikowski International Corp, Malakoff, Tex. The alumina was suspended in distilled Milli-Q Plus™ water by sonication. The highest grade of reagents available were used. All solutions were prepared with distilled, deionized Milli-Q Plus water. All solutions used for nucleic acid work were sterilized by autoclaving or by filtration through a 0.22 µm filter. Exposure of labeled DNA to light was minimized by using opaque siliconized glassware, aluminum foil covering, or reduced room lighting conditions.

BAC clone samples and unlabelled cDNA probes can be prepared using procedures described previously. The BAC system is based on the well-studied *Escherichia coli* F factor. The BAC system allows the cloning of large DNA from a variety of complex genomic sources into bacteria, where the DNA is stable, easy to manipulate, and represents a single foreign DNA source.

Figure 11:
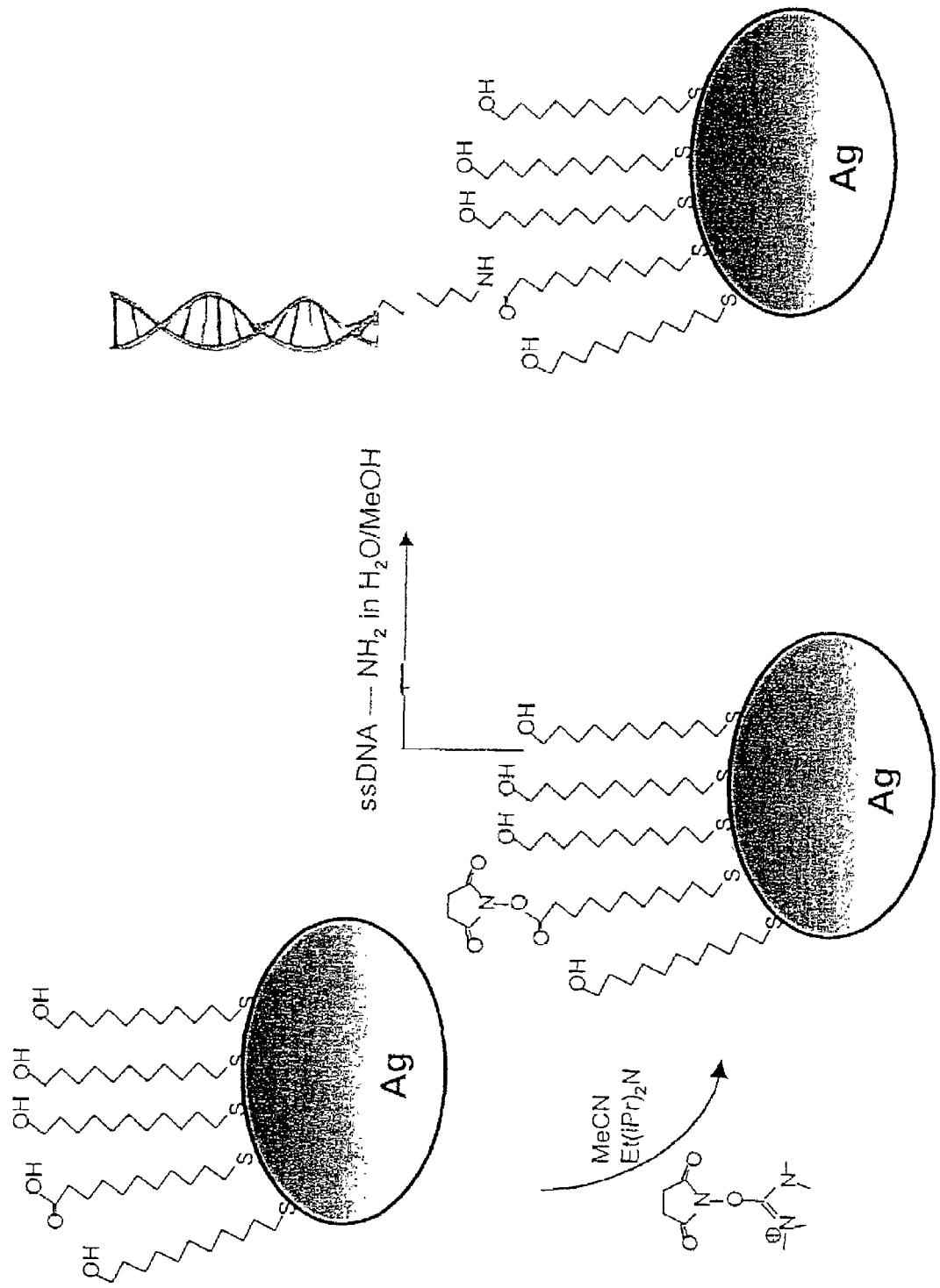
FIG. 11 shows a method for binding DNA to a silver nanoparticle.
Figure 12:
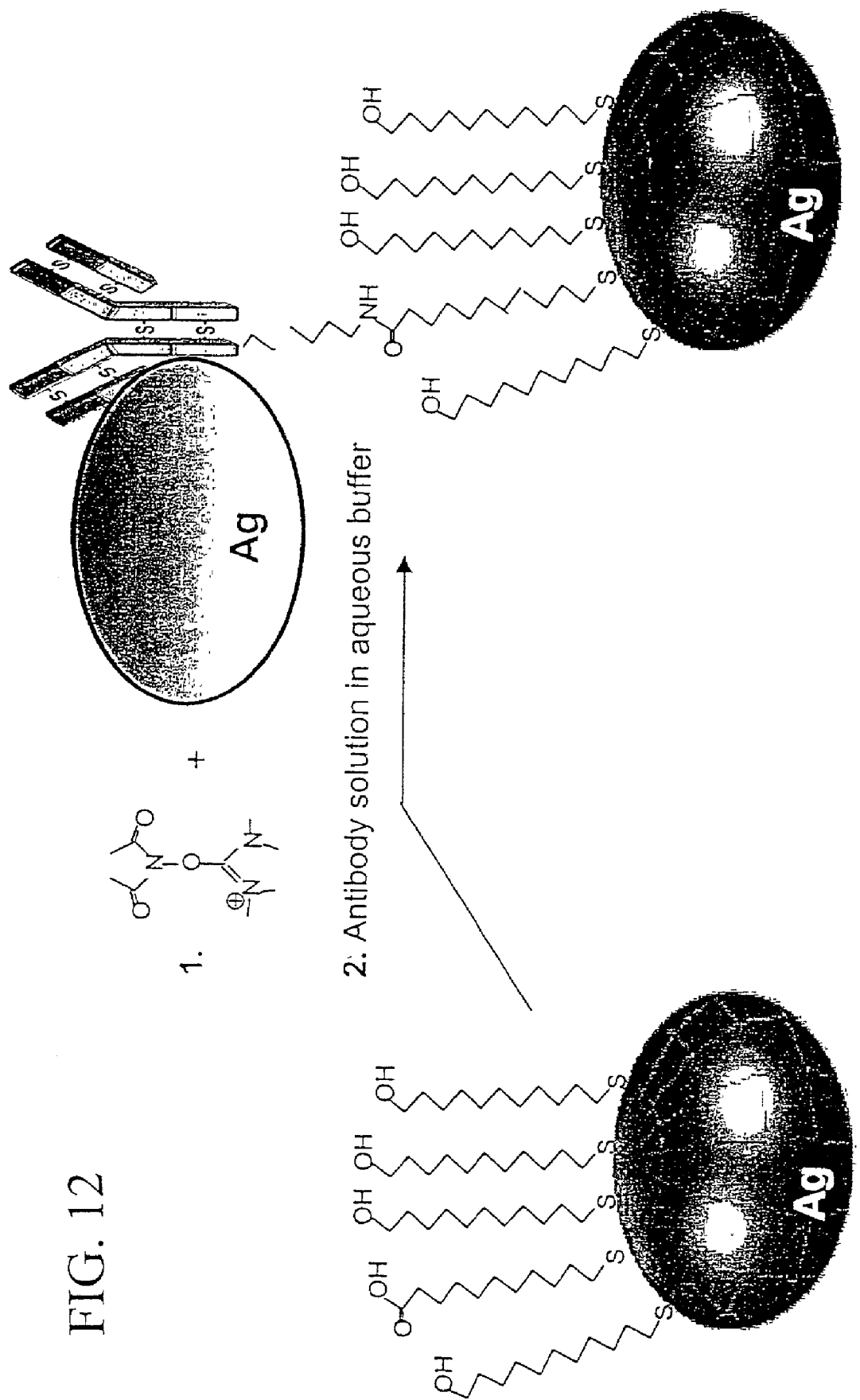
FIG. 12 shows a method for binding an antibody to a silver nanoparticle.
Figure 13:
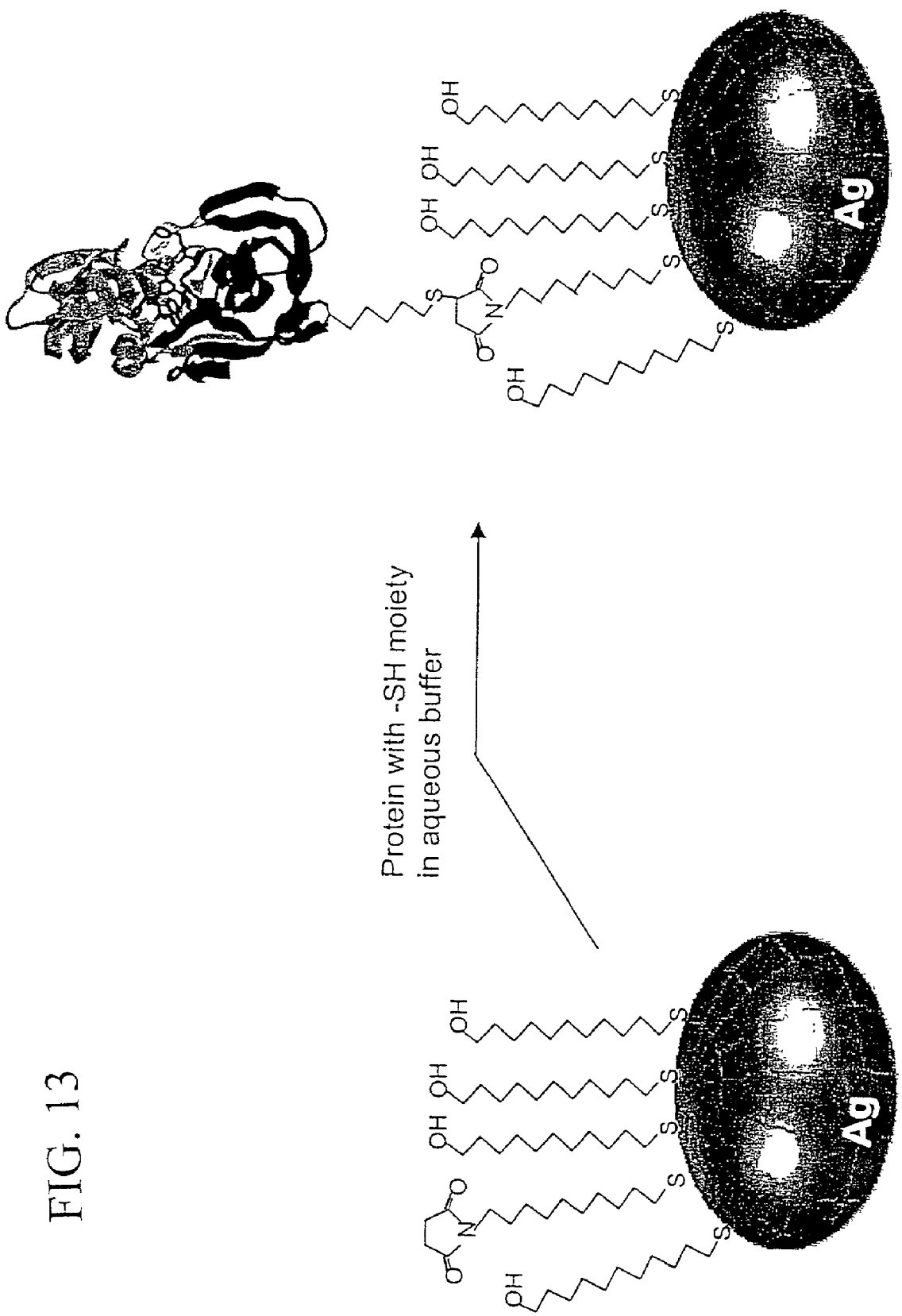
FIG. 13 shows a method for binding a protein to a silver nanoparticle.

In the present invention, silver nanoparticles have generally been used to form the SERS active platform. Several coupling approach used to bind various receptor probes to silver nanoparticles are shown in FIGS. 11-13. This coupling can involve esterification under mild conditions of a carboxylic acid with a labile group, an N-hydroxysuccinimide (NHS) derivative, and further reaction with free amine groups in a polypeptide (enzymes, antibodies, antigens, etc) or amine-labeled DNA, producing a stable amide. Boncheva, M.; Scheibler, L.; Lincoln, P.; Vogel, H.; Akerman, B. Langmuir 1999, 15, 4317-20.

NHS reacts almost exclusively with primary amine groups. Covalent immobilization can be achieved in as little as 30 minutes. Since $H_2O$ competes with $NH_2$ in reactions involving these very labile esters, it is important to consider the hydrolysis kinetics of the available esters used in this type of coupling. The derivative of NHS used in FIG. 11, O-(N-succinimidyl)-N,N,N',N'-tetramethyluronium tetrafluoroborate, increases the coupling yield by utilizing a leaving group that is converted to urea during the carboxylic acid activation, hence favorably increasing the negative enthalpy of the reaction.

In the method shown in FIG. 11, silver nanoparticles are provided having COOH end-group functionality. A linker, such as MeCNEt(iPr)$_2$N is then bound to the silver nanoparticle through attachment to the COOH group. Single stranded DNA is then added to the silver containing nanoparticle. Hybridization is then accomplished by providing a complementary labeled probe to the single stranded DNA added in the previous step.

FIG. 12 shows a method for binding antibodies to metal nanoparticles starting with silver nanoparticles having COOH end-group functionality. Following attachment of a linker, antibodies can be attached to the linker by providing an antibody solution in an aqueous buffer.

FIG. 13 shows a method for binding protein to metal nanoparticles starting with silver nanoparticles having COOH end-group functionality. Following attachment of a linker, protein can be attached to the linker by providing a protein solution with —SH moiety in an aqueous buffer.

RASERS Platform Adaptable for Biochip

Figure 14:
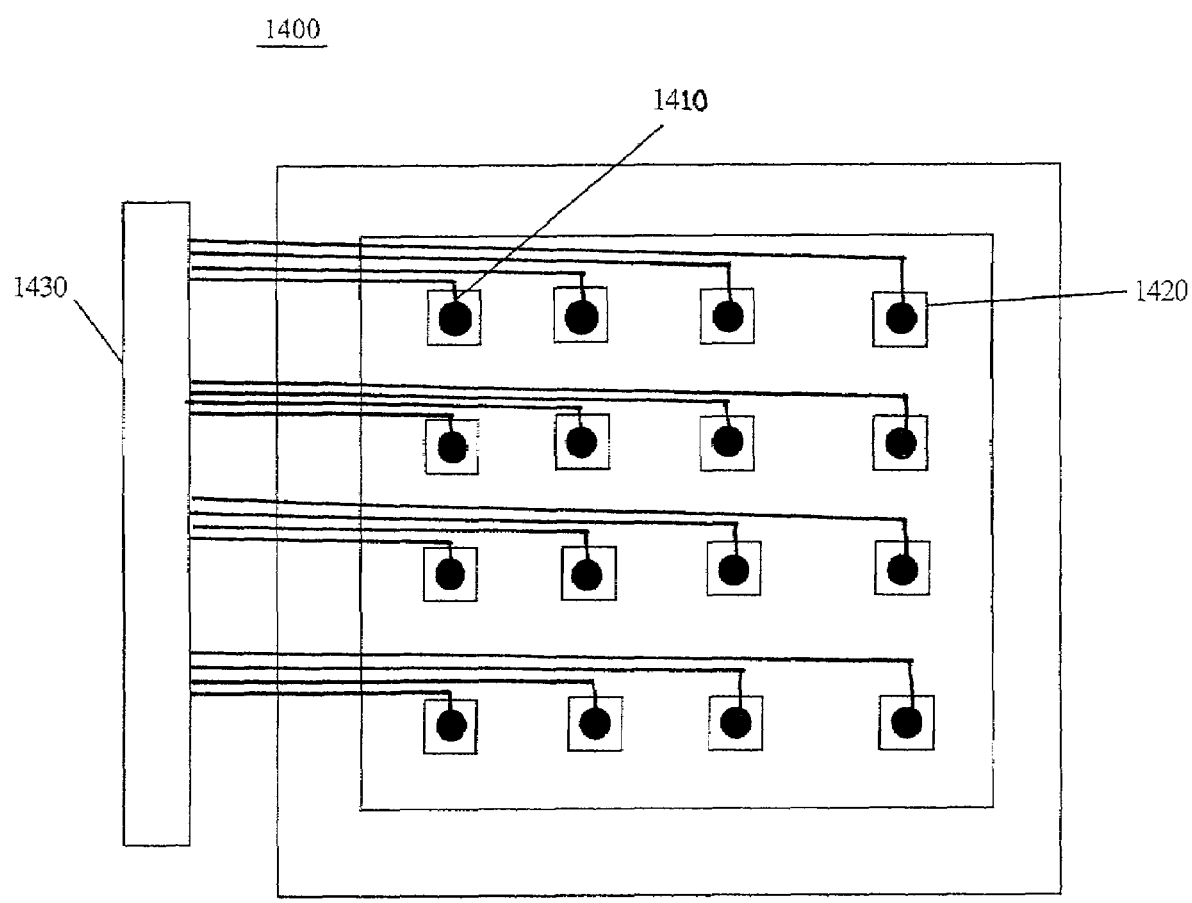
FIG. 14 shows a randomly addressable SERS (RASERS) platform, according to an embodiment of the invention.

The SERS platform can be configured as a randomly-addressable SERS (RASERS) microarray platform which can be provided through formation of a microelectrode array. Referring to FIG. 14, RASERS platform 1400 can be used to modulate the Raman/SERS signal through application of a bias voltage using a microarray control system 1430. RASERS platform 1400 can be used with a SERS Biochip.

Exemplary RASERS microarray platform 1400 includes sixteen (16) electrically conductive microelectrode array elements 1410 which are each disposed on sensors 1420. Although FIG. 14 shows a 4×4 electrode array, other array sizes and arrangements are possible. In addition, even though each microelectrode element 1410 is shown having its own sensor 1420, a single sensor 1420 can support a plurality of microarray elements, such as all 16 shown in FIG. 14. Although not shown, a plurality of receptor probes, such as bioprobes, are disposed on microelectrode elements 1410.

A metal, such as silver may be used to form microelectrode array elements 1410 for this purpose. Silver at an electrode can be oxidized by the reaction $Ag \rightarrow Ag^+ + e-$ during the first half of the cycle through application of an appropriate potential. During the reduction half cycle, a roughened silver surface is reproduced by the reduction reaction $Ag^+ + e- \rightarrow Ag$.

This oxidation-reduction procedure generally produces surface protrusions in the size range of 25 to 500 nm on the electrode surface. The working electrode is generally placed in a position such that excitation source energy (e.g., from a laser) can be focused onto its surface and the Raman scattered light can be efficiently collected by appropriate detection optics. Strong SERS signals generally appear only after an electrochemical oxidation-reduction cycle, often referred to as "activation cycle", is performed on the metal electrode. Thus, a weak signal is observed after the oxidation half cycle, and a strong signal after the reduction half cycle. For some microarray materials, it may be possible to cycle a plurality of times between oxidized and reduced states.

RASERS can provide several advantages. RASERS can provide two independent methods for detection. Both voltametric detection using microelectrodes and optical detection using SERS may be used.

The microelectrodes 410 can be used to move and concentrate biomolecules that are themselves generally charged species. Other metal electrodes such as platinum can also be used as SERS substrates. Experimental factors such as the influence of laser illumination of copper electrodes during oxidation/reduction treatment on SERS signals of pyridine and benzotriazole have been investigated. Photoalterations of the copper electrode can result in a further ten-fold increase in the SERS signal.

A biochip having electrodes is disclosed in U.S. Pat. No. 6,331,274 to Ackley, et al. (Ackley) is entitled "Advanced active circuits and devices for molecular biological analysis and diagnostics." Ackley discloses devices for performing active biological operations which utilize various structures to advantageously collect and provide charged biological materials to an array of microlocations. An active biological matrix device includes an array of unit cells, each unit cell including a variable current control element, a select switch, and a return electrode. The output of the select switch is preferably adapted to contact a conductive solution including charged biological materials. The return electrode is preferably connected to a second potential and adapted to contact the conductive solution.

Use of Raman spectroscopy is not disclosed or suggested by Ackley. The Ackley biochip is a matrix that allows users to put controlled positive and negative electrical charges on electrodes at specific locations on the chip, creating the potential to move molecules around at will, since DNA is a negatively charged molecule. Thus, the design, operating principle, use, detection, applications of the RASERS platform described herein is quite different from the platform disclosed by Ackley.

The RASERS platform can be based on a SERS-active conducting polymer. This substrate can consist of a metallurized polymer film. Silverized polyvinyl alcohol (PVA) can be deposited on a solid support, such as glass microscope slide. The characterization of the substrates were investigated using cresyl fast violet. Analytical figures of merit were also investigated.

Polyvinyl alcohol silver films were prepared according to processing known in the art. 0.45 g $AgNO_3$ was directly added to 6 mL of 10% w/w aqueous solution of polyvinyl alcohol (mw 100,000) and stirred at room temperature for 24 h. The resulting viscous solution was stable for at least several weeks.

The SERS active substrates were prepared by spin-coating of PVA-Ag solution on glass plates after mixing with 5% w:w aqueous suspension of alumina in 1:5 ratio. The prepared slides were dried under ambient conditions for one day and then further dried in an oven at 80° C. for one hour. The reduction of silver to metallic silver was done by inserting the coated plates in 4% w/w solution of $FeSO_4$ for 3 minutes. The reduced films were then washed with water and dried at 100° C. for 5 minutes. A masking step was then be used to form the microarray.

Microfluidics Based System

In another embodiment of the invention, a microfluidics-based SERS system is described. A SERS biochip device can be designed to have a microfluidic sample delivery system which can be integrated with a sampling platform. For example, applied to a SERS biochip, microfluidics can provide fast sample manipulation and on-chip detection. Microfluidic devices can include a capillary electrophoresis array, a liquid chromatography array, a gas chromatography array, or a lab-on-a-chip system.

The microfluidic system can be used to provide biological samples and/or reagents to the sampling platform via a microfluidic sample delivery system. The microfluidics system can also be designed to deliver silver, gold, or other metal nanoparticles or reagents to provide the same onto a sampling or sampling/detection platform.

Figure 15:
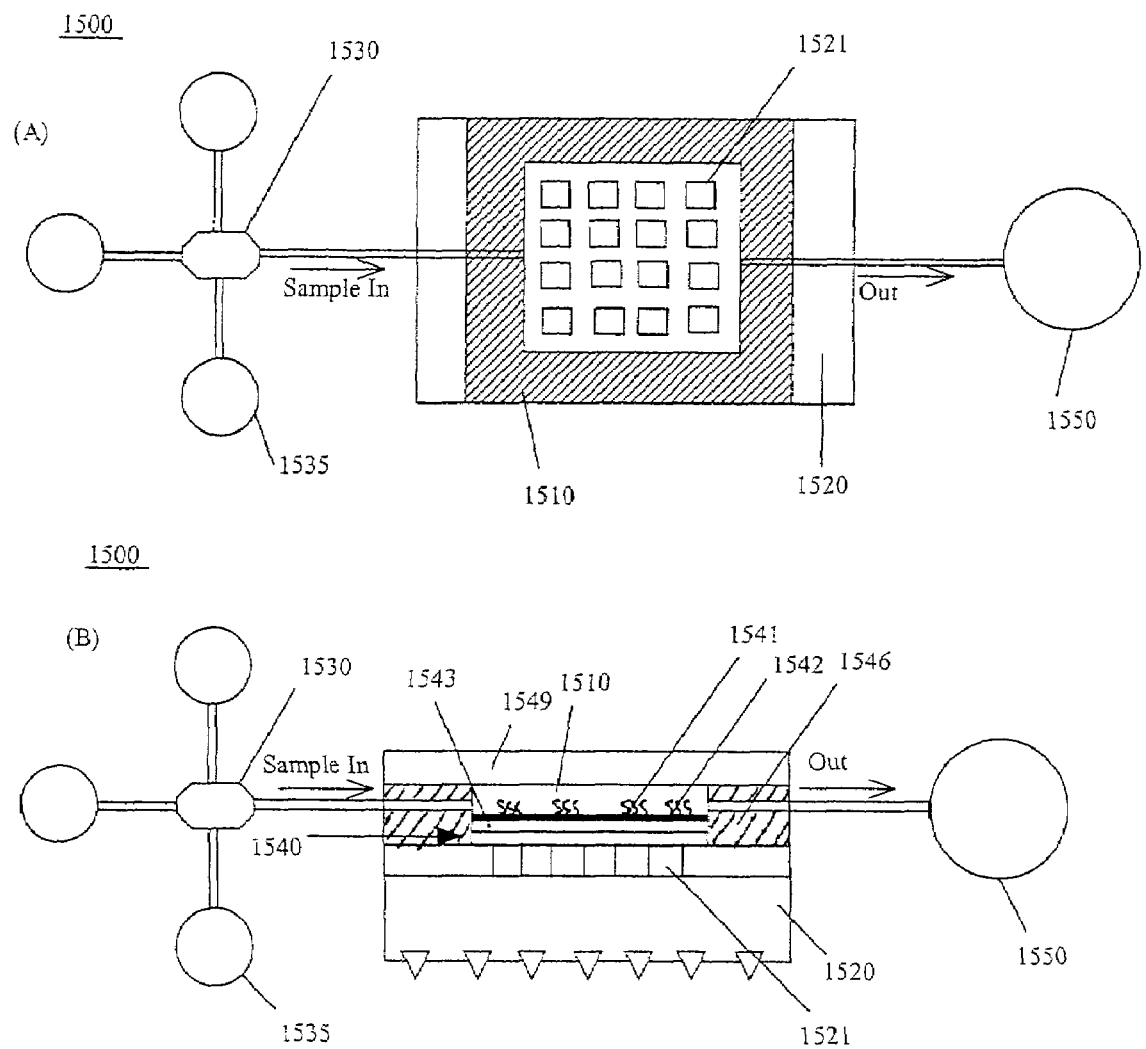
FIGS. 15(A) and (B) show a top view and a side view, respectively, of a single chamber microfluidics system adapted to supply analyte containing fluids to a sampling platform disposed on a biochip.

FIGS. 15(A) and (B) show a top view and a side view, respectively, of a biochip 1500 including single chamber microfluidics system. Microfluidics system includes fluid (e.g. reagent or sample) reservoirs 1535 which are fluidically connected to microfluidics controller 1530 which supplies fluids to sampling platform 1240. Microfluidic controller 1530 controls the flow of fluids to biochip 1200. Sampling platform 1540 includes bioprobes 1541 which are disposed on SERS-active surface 1542, the SERS-active surface 1542 disposed on a substrate material-. 1543. Substrate 1543 can be formed from materials including plexiglass, plastics, gels, polymers glass, silica and silicon wafers. A wavelength selection filter 1546 can be disposed between substrate 1543 and microchip 1520. Reservoir 1550 receives fluid output after flowing over sampling platform 1540.

Microchip 1520 includes a plurality of photodetectors 1521. The sampling chamber 1510 including its sample delivery channels (not shown) can be micromachined into substrate 1543. Glass or quartz slides can be affixed to the top 1549 of the substrate 1543 seal the sampling chamber 1510 to serve as an excitation window.

Several binding techniques can be used to seal the sampling chamber 1510. For example, glue, vacuum cement, or elastic bands can be used for this purpose. The sampling chamber 1510 can be formed by drilling holes into a block of suitable substrate material. Drilling can be performed using a conventional drill or a laser drill. For example, a 1 cm×1 cm hole can be drilled through the center of the substrate block. The network of microfluidic channels can consist of series of 1-mm diameter holes are drilled from opposite edges of the substrate (e.g. plexiglass) slab to the central sampling chamber.

The temperature of the sampling platform can be controlled using heating wires or a thermoelectric system. The microfluidic device can be mounted directly onto the sensing microchip 1520 as shown in FIG. 15(B). SERS signals from the sample arrays on the sampling platform can be collected from the back side of the platform and projected through the bottom window and wavelength selection filter 1546 onto the sensing microchip 1520. The wavelength selection filter 1546 is preferably a sharp-edge cut-on filter for rejection of the laser line followed by an appropriate Raman selection filter.

Micropump systems commercially available (e.g., Astoria-Pacific, Clackamas, Oreg., Model 302A micropump module) can be used to deliver sample and reagents. The micropumping system can be connected to the microfluidic sampling chamber via an array of microtubing. Each tube is inserted directly into a sample delivery channel of the Plexiglas. The other end of each tube is readily coupled to a host of fixtures that permit controlled delivery of a multitude of reagents or samples into the inlet ports of the sampling chamber.

Prior to flushing the sampling chamber with a sample, a sampling platform (e.g. nitrocellulose membrane), which contains an array of capture probes, such as proteins or single-stranded DNA fragments, is placed in the chamber. The various capture probes are independently anchored at specific areas of the SERS-active platform which are aligned with the detection elements of the IC biochip.

Another embodiment of a microfluidic system 1600 is shown in FIGS. 16(A)-(B). FIG. 16(A) is a top view of system 1600, while FIG. 16(B) is a bottom view of the same. Microfluidics system 1600 includes multiple independent microchannels. An array of microchannels can be formed on the top 1611-1618 and the bottom 1621-1628 in a suitable substrate 1610, such as plexiglass, plastic, glass, silver or quartz, where both reactions and detection take place. Each microchannel has an associated microchamber, such as microchamber 1631 shown in FIGS. 16(A) and 16(B).

The microfluidic system 1600 shown can provide a separate microchamber 1631 for each detection element (not shown). For example, microfluidic system 1600 has sixteen separate microchanels and microchambers, these microchannels and microchambers capable of supplying a separate fluid pathway to and from each sensing location provided by a 4×4 biochip array.

A wafer (e.g. Si) can be etched from both the top side and the bottom sides to form microchannels and microchambers on each side. Each chamber can have a sample/reagent inlet channel and an outlet channel. The channel patterns (e.g., 50-mm width) can be etched on multiple layers of a silicon wafer and then the layers stacked with the microchamber holes aligned from one layer to the next. The depth of the microchannels are preferably less than half of the width of the wafer, so that the channels etched on the top side of the wafer are not connected to the channels etched on the bottom side of the wafer.

A microchamber array device can be composed of 3 stacked silicon wafers. The top wafer can serve as a cover transparent to the excitation light that enters from the top. The bottom wafer is transparent to the SERS signal that is transmitted to the sensor array of the microchip under it. Each layer can include a pattern of 700 μm diameter holes with sufficient center-to-center spacing to avoid overlap. For example, 1 mm center-to-center spacing is generally appropriate for 700 μm holes. In this configuration, the spacing between two adjacent sensors is approximately 300 mm and can have four 50 mm-diameter microchannels. The hole pattern is preferably centered on the wafer.

The micro-machined channels each serve as a reagent/sample inlet to a separate microchamber. The 50 μm width (or diameter) channels are machined from the wells to one of two opposing edges of the wafer. Each opposing edge houses eight sample/reagent inlet ports. The sample delivery system is similar to that described for the single-chamber design. A combination of shut-off valves, tee joints with micro-splitter valves, and 6-port injection valves will permit the independent delivery of a wide range of samples and reagents to each microchamber, and hence allow the execution of independent reaction procedures in each independent microchamber. Note that once the master plate is produced using etching procedures on silicon wafer, it is possible to make a stamping matrix to produce large quantities of the microfluidics device using plastics and polymer materials.

Continuous Monitoring System

Figure 17:
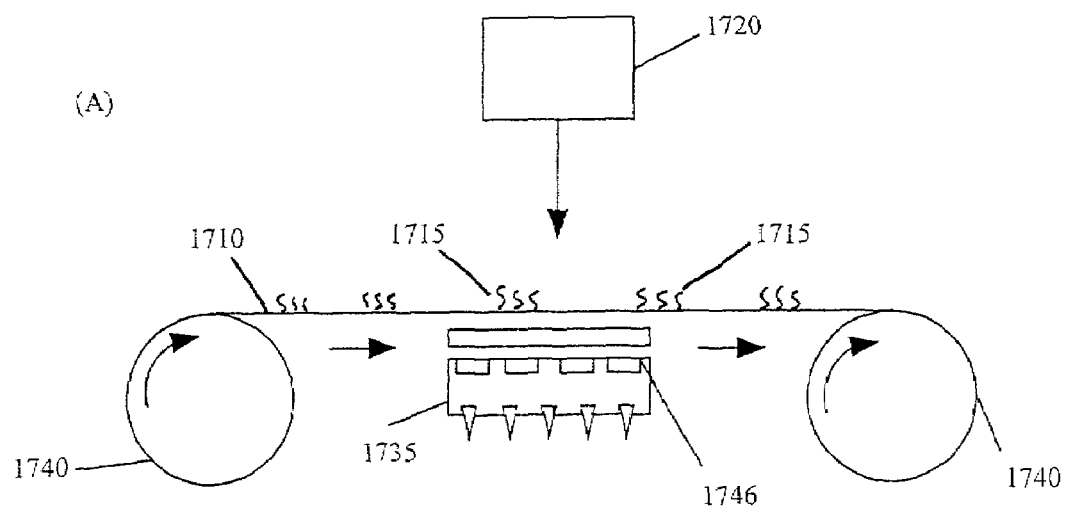
FIGS. 17(A) and (B) shows continuous monitoring SERS biochip having a integrated detection system and a non-integrated detection system, respectively, according to another embodiment of the invention.
Figure 17:
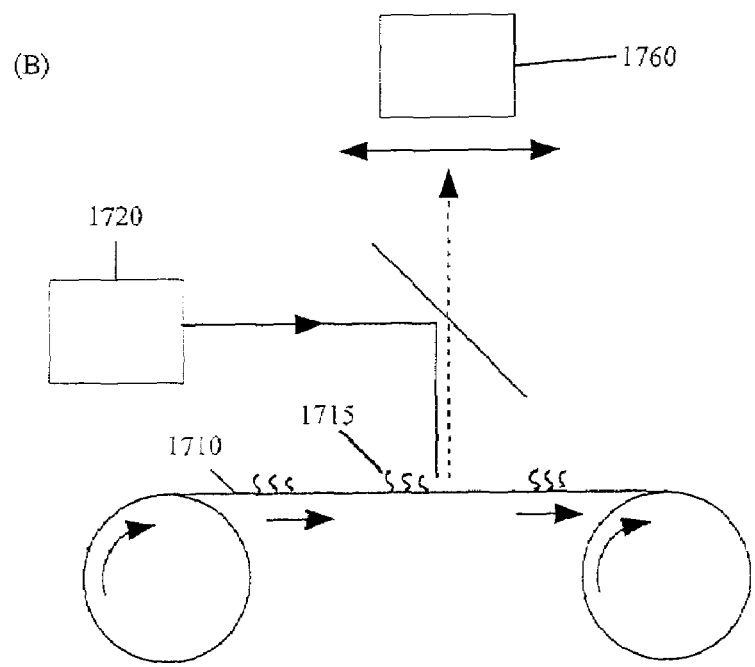

The sampling platform can also be configured as a continuous monitoring SERS system, such in the SERS biochip system 1700 shown in FIG. 17(A). In this configuration a SERS-active continuous tape or membrane 1710 containing arrays of receptor probes 1715 distributed thereon is moved into alignment with the excitation light source 1720 and a detector, such as an integrated detector array such as a SERS microchip 1735, having a plurality of detector elements 1746 using a translation apparatus 1740. Although a SERS microchip detector array 1735 is shown, the detector array can be a non-integrated detector array. The translation apparatus 1740 can be a reel-to-reel, or similar apparatus. The sampling platform section analyzed can be renewed by subsequently moving a new portion of the tape into the detection area.

FIG. 17(B) shows a continuous monitoring SERS system 1750 including nonintegrated detector 1760. In this system, optical filter 1755 directs light received from excitation source 1720 to receptor probes 1715. Raman scattered light scattered by bioprobes 1715 is passed by filter 1755 for measurement by detector 1760.

EXAMPLES

Example 1

SERS Biochip System

To demonstrate operation of a SERS biochip system, experiments were conducted to evaluate the detection capability of biotargets using a biochip having a SERS sampling platform and SERS detection apparatus. Alumina nanoparticle-based SERS platforms were prepared as follows. Three drops of a 5% aqueous suspension of the alumina were dropped and spread evenly on the surface of a pre-cleaned rectangular glass strip (2.5 cm×1.25 cm; 1 mm thick) cut from a microscope slide. The glass strip was then placed on a spinning device and spun at 2000 rpm to spread the alumina uniformly. Next, a 100-nm layer of silver was thermally evaporated onto the alumina-coated glass strip at a pressure of $2 \times 10^{-6}$ Torr 0.45 g of $AgNO_3$ was added to 1.56 g of 10%(w/w) aqueous solution of PVA and stirred at room temperature for 24 h. The resulting solution was spin-coated on glass plates. The resulting platforms were subsequently dried in an oven at 100° C. for 1 hour. The dried platforms were dipped into $FeSO_4 \cdot 7H_2O$ (4% w/w) solution and then dried in an oven at 100° C. for 15 min.

SERS-active labels were coupled to DNA probes using the EDAC [1-ethyl-3,3-dimethylaminopropyl carbodiimde] coupling procedure, but with significant changes to improve coupling efficiency and yield of recoverable DNA. A 1:1 molar ratio of DNA and EDAC was used in the initial reaction to avoid extensive cross-linking which can occur if there is an excess of EDAC. The DNA probe material was incubated with the SERS-active dye for approximately 3-4 hours, as this shorter period of incubation resulted in less insoluble material being formed during the course of the dye-labeling reaction.

A series of experiments were carried out to investigate the suitability for DNA labeling of the following SERS-active compounds: cresyl fast violet (CFV) and brilliant cresyl blue (BCB). BAC clone DNA (a cDNA obtained from a bacterial artificial chromosome), herring sperm DNA (Gibco/BRL), and herring sperm DNA labeled with CFV or BCB were bound to wells of an InterMed Nunc-Immuno Maxisorp 96 well Plate using Reacti-bind DNA Coating Solution (Pierce, Rockford, Ill.). A volume of 200 femtoliters of Reacti-bind was mixed with approximately 100 ng of DNA (10 femptoliter in a well, and was allowed to incubate over night at room temperature. After the incubation, unbound DNA and Reacti-Bind solution was washed away with three rinses of PBS. Reacti-Bind was chosen to bind DNA to the plastic microwell surface since this procedure appeared to be a simple scheme which would bind BAC clone DNA without modification of the BAC clone DNA itself. The BAC clone DNA was not modified so as to introduce a free amino group on either end of the DNA strand.

Desired strands of oligonucleotides were synthesized and labeled with Raman or SERS labels, such as Cy5 dyes, using known methods. All oligonucleotides were synthesized using an Expedite 8909 DNA synthesizer (Millipore). Fluorescein-labeled oligonucleotides were prepared with fluorescein CPG columns (for 3' labeling) or fluorescein phosphoramidite (for 5' labeling) using modified synthesis protocols as recommended by the manufacturers. Oligonucleotides with amino linkers were synthesized using either C3 aminolink CPG for 3' labeling or 5' amino modifier C6 (Glenn Research, Sterling, Va.) for 5' labeling. All oligonucleotides were synthesized using Expedite reagents (Millipore) and were de-protected and cleaved from the glass supports using ammonium hydroxide. The de-protected oligonucleotides were concentrated by evaporating the ammonium hydroxide in a Speedvac evaporator (Savant) and resuspended in 100 μL distilled $H_2O$. Further purification was performed by isopropanol precipitation of the DNA as follows: 10 μL of 3 M sodium acetate pH 7.0 and 110 μL isopropanol was added to 100 μL solution of DNA. The solution was then frozen at −70° C.

Sodium acetate was used instead of ammonium acetate since the residual ammonium ions interfere with Cy5 linkage as well as with binding of DNA to solid supports through the amino linkers. The precipitate was collected by centrifugation at room temperature for 15 min and was washed 3 times with 50% isopropanol. Residual isopropanol was removed by vacuum drying in the Speedvac and the DNA resuspended in sterile distilled water at a final concentration of 10 μg/μL. These stock solutions were diluted in the appropriate buffer at a 1:10 dilution to give a DNA concentration of 1 μg/μL.

SERS-labeled probes were synthesized as follows. Solutions of BCB (Allied Chemical) and CFV (Fluka) were prepared at 0.15-0.25 M concentrations. Labeled oligonucleotides were synthesized as 5'-phosphoramidates using known methods. Briefly, solutions of deoxyribonucleotide oligomers (either 9 or 18 residues in length; Sigma) were converted to 5'-phosphoroimidazolide intermediates with 0.2-M imidazole pH 6.0 and 0.5 M 1-ethyl-3,3-dimethylaminopropyl carbodiimide by incubation at 50° C. for 3 hours. The 5'-phosphorimidazolides were then reacted with equal volumes of the SERS-active labels (e.g., cresyl fast violet dye) for 18 hours at 50° C. Unreacted label was removed from the reaction mixture by gel filtration on Bio-spin 6 columns (Bio-Rad Laboratories Hercules, Calif.). The resultant labeled oligonucleotide samples were concentrated by lyophilization.

For labeling DNA with Cy5 dye (Amersham Life Sciences Buckinghamshire UK), modified oligonucleotides containing alkyl amino groups were derivatized as follows: 30 pmoles of the DNA was dissolved in 250 μL 0.5 M sodium chloride and passed through a Sephadex G10 (1 cm diameter, 10 cm long) (Pharmacia, Peapack, N.J.) column equilibrated with 5 mM borate buffer (pH=8.0). The void volume containing the oligonucleotide was collected and concentrated by evaporation. This was dissolved in 100 μL 0.1 M carbonate buffer (pH=9.0). Cy5 (1 mg in carbonate buffer) was added to the oligonucleotide and the conjugation reaction was performed at room temperature for 60 min with occasional mixing. The conjugated oligonucleotide was separated from the free dye using a Sephadex G10 column as described above. The fractions containing the labeled DNA were collected and concentrated using a Speedvac evaporator.

Measurements using the SERS biochip were performed using a biochip device with 4×4 photodiode array for simultaneous detection of a variety of SERS dye and SERS-labeled DNA probes. The signals from the photodiodes were directly recorded without the need of any electronic interface system or signal amplification device. The signal of each sensing of the microchip was transmitted directly into a digital photometer or a strip chart recorder. The data from the photometer were linked to a personal computer (PC) via an RS-232 link. The sampling platform of the biochip contained microspots of SERS-labeled DNA.

Figure 18:
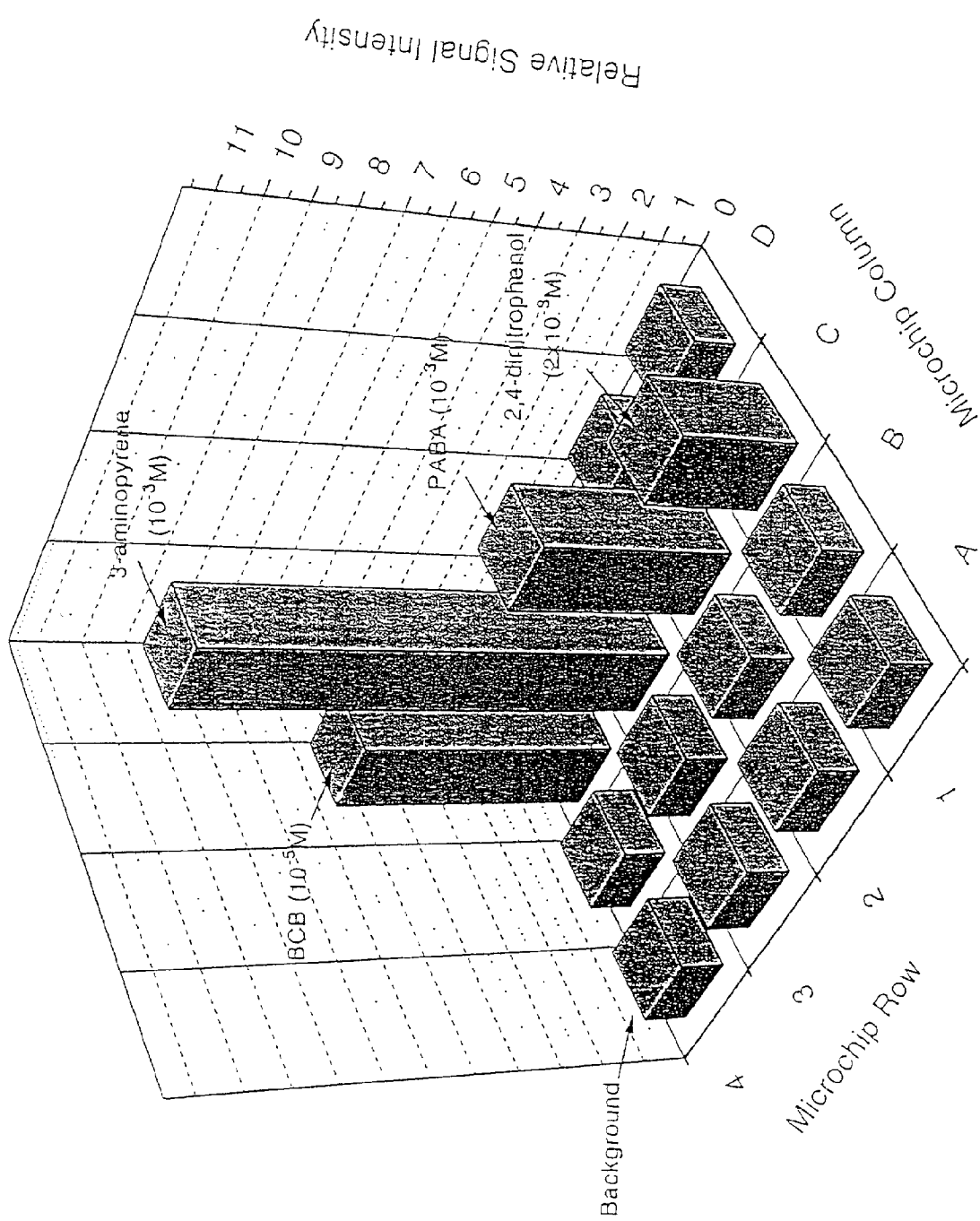
FIG. 18 shows SERS signals detected from a biochip comparing detected levels using various dyes, and in one instance, no dye.

Several series of measurements were used to evaluate the SERS biochip. In the series of measurements, the capability of the SERS biochip to detect SERS signals was demonstrated. Sample solutions of various SERS-active dyes were spotted directly onto the SERS-active sampling platform of the biochip. The spots were subsequently measured using the SERS biochip for detecting the Raman signal. FIG. 18 shows the SERS signals detected from the biochip using p-amino benzoic acid, dinitrophenol, 3-aminopyrene and BCB dye. The signals of the biochip with no dye showed a low level of background signals, whereas stronger signal were produced by DNA including respective dyes.

Figure 19:
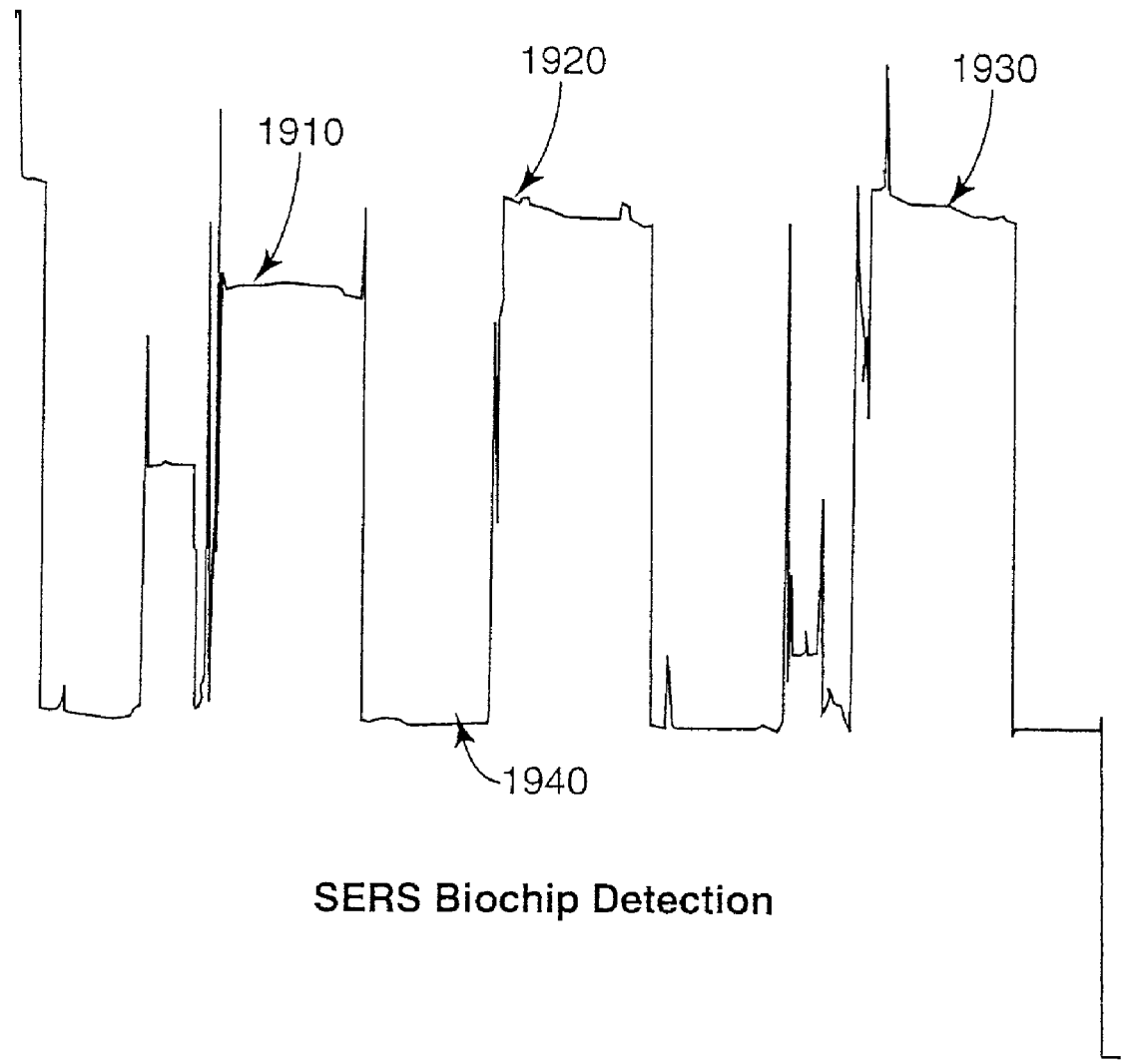
FIG. 19 shows detected SERS signals from CFV labeled DNA.

The second series of measurements were performed to demonstrate the biochip performance with the measurements of SERS labeled DNA samples. This measurement series was designed to demonstrate that the fluorescence signal from the sample and substrate did not interfere with the SERS measurement using the biochip. Samples tested were CFV-labeled DNA from BAC clones and CFV-labeled BAC DNA from Herring sperm. FIG. 19 show that the SERS signal levels 1910, 1920 and 1930 detected by the biochip from these samples had amplitudes significantly higher than the background signal 1940.

Example 2

Platform Based on Metal Nanoparticles Embedded in Sol Gels

Biochip sampling platforms can be made using SERS-active sol gel materials preformed in desired sampling devices. (M. Volkan, D. L. Stokes and T. Vo-Dinh, J. Raman Spectroscopy, 30, 1057, 1999). The controlled precipitation of silver chloride was achieved by the reaction of silver nitrate with trichloroacetic acid which leads to a slow release of chloride ions. Silver chloride particles were reduced to silver nanoparticles by $FeSO_4 \cdot 7H_2O$. The sol-gel films prepared exhibit good optical properties and induce a strong SERS effect for several model compounds, including cresyl fast violet (CFV) and brilliant cresyl blue (BCB). Precursor sols were prepared by hydrolysis of TEOS (Tetra ethyl orthosilane) and MTEOS (methyltriethoxysilane) in water/ethanol solution, using $HNO_3$ as a catalyst. $AgNO_3$ (silver nitrate) and $CCl_3CO_2H$ [trichloroacetic acid (TCAA)] were added in various ratios. The final coating solution had the following composition: 1.3 mL TEOS, 1.3 mL MTEOS, 5.3 mL ethanol, 0.8 mL of water, 1.3 mL ethylene glycol (EG), 1.5 mL 3-M $AgNO_3$, 0.5 mL 3-M TCAA (Ag:Cl,1:1), and 0.03 mL concentrated $HNO_3$. FIG. 20 shows the effectiveness of this sol gel substrate for the crystal fast violet (CFV) dye ($10^{-5}$ M) that has been used as the DNA label in studies performed. Laser power provided was 6 mW at 632.8 nm.

Example 3

Platform Based on Metal Nanoparticles Embedded in Polymer

Figure 16:
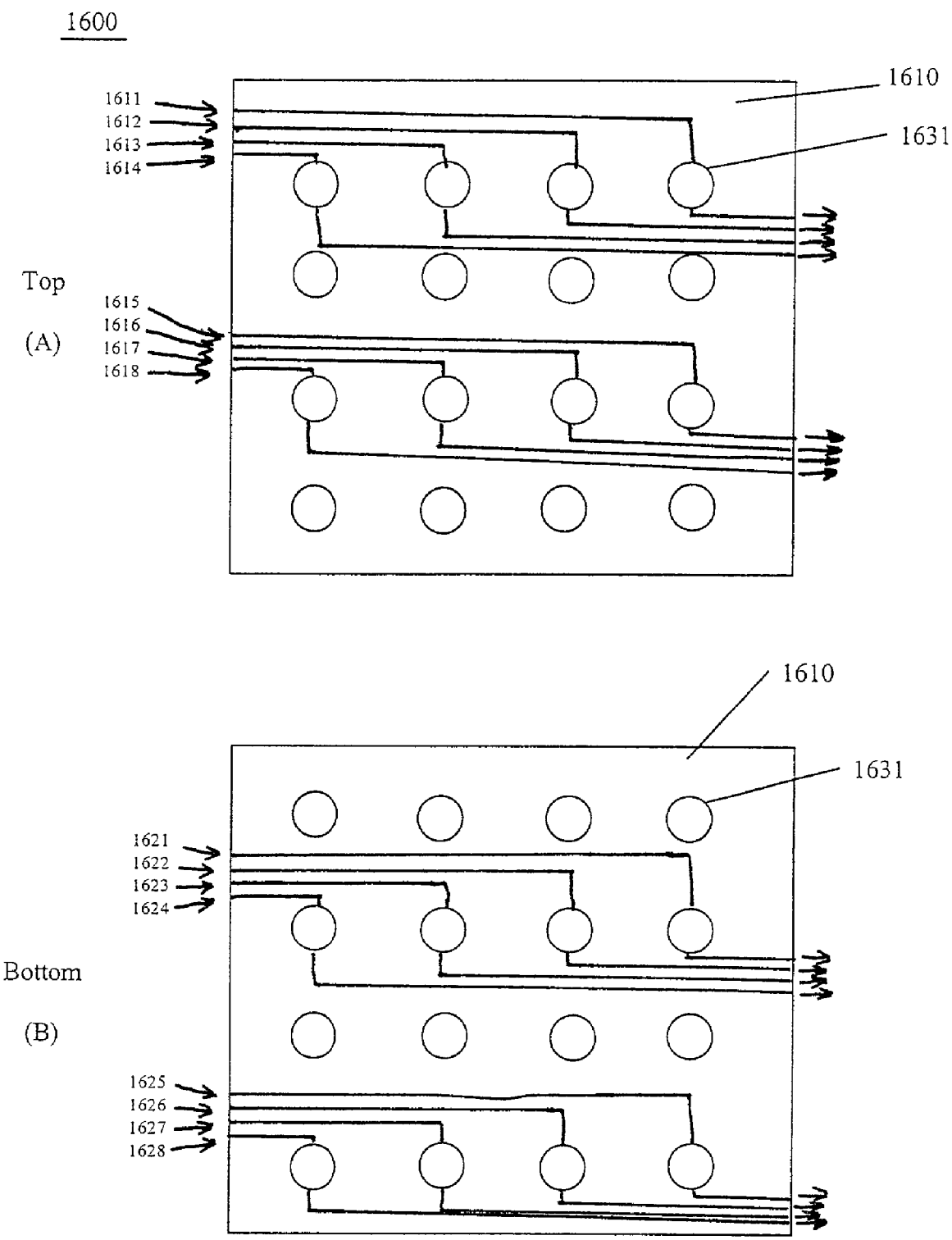
FIGS. 16(A)-(B) show a top view and a bottom view, respectively, of a multiple chamber microfluidics system adapted to supply analyte containing fluids to a sampling platform.

A SERS-active polymer substrate that included a polyvinyl alcohol (PVA) matrix embedded with isolated silver nanoparticles was tested. The silver nanoparticles were reduced from silver nitrate mixed within the PVA matrix. The PVA-based substrates were prepared in the following manner: 0.045 g of $AgNO_3$ was added to 1.56 g of 10% (w/w) aqueous solution of PVA. The mixture was stirred at room temperature for 24 h. The resulting solution was spin-coated on glass plates (prepared from microscope slides as described above). The coated plates were subsequently dried in an oven at 100° C. for 1 h Prior to SERS measurements, dried substrates were finally dipped into $FeSO_4 \cdot 7H_2O$ (4% w/w) solution and again dried in an oven at 100° C. for 15 min. FIG. 16 shows the detection of a BAC clone DNA labeled with CFV using the PVA SERS platform.

Example 4

Sensitivity of SERS

Recent improvements have been achieved towards the goal of single molecule detection of cresyl fast violet (CFV) via Raman scattering using nanostructed solid substrates (Stokes, Hueber et al, 1998). These improvements are due to the optimization of a silver island substrate which imparts a large surface-enhanced Raman scattering (SERS) enhancement. Furthermore, a He—Ne laser enables obtaining an additional resonance enhancement factor, again raising the signal level.

In the experiment performed, the detection system utilized a spectrograph equipped with a red-enhanced intensified CCD (RE-ICCD). A confocal excitation/collection geometry was implemented with a 100× objective lens. The 0.9 numerical aperture of this lens helped ensure a tight focus and efficient scattered signal collection. The SERS spectrum of CFV which was obtained from a $5 \times 10^{-11}$ M solution. A 1-µL aliquot ethanolic CFV solution (i.e., $3 \times 10^7$ molecules) was spotted on the solid SERS platform and allowed to dry after spreading to a 6.5 mm diameter. The broadness of the 595 $cm^{-1}$ band of this spectrum results from the use of a 500-µm entrance slit width to improve signal collection. Assuming a laser spot diameter of 10 µm and even distribution of CFV molecules within the 6.5-mm diameter spot, the number of probed molecules was estimated to be approximately 70.

The results showed SERS signals from fewer than 30 molecules. The limit of detection of one molecule detection is possible.

Example 5

SERS Microelectrodes for RASERS

Figure 21:
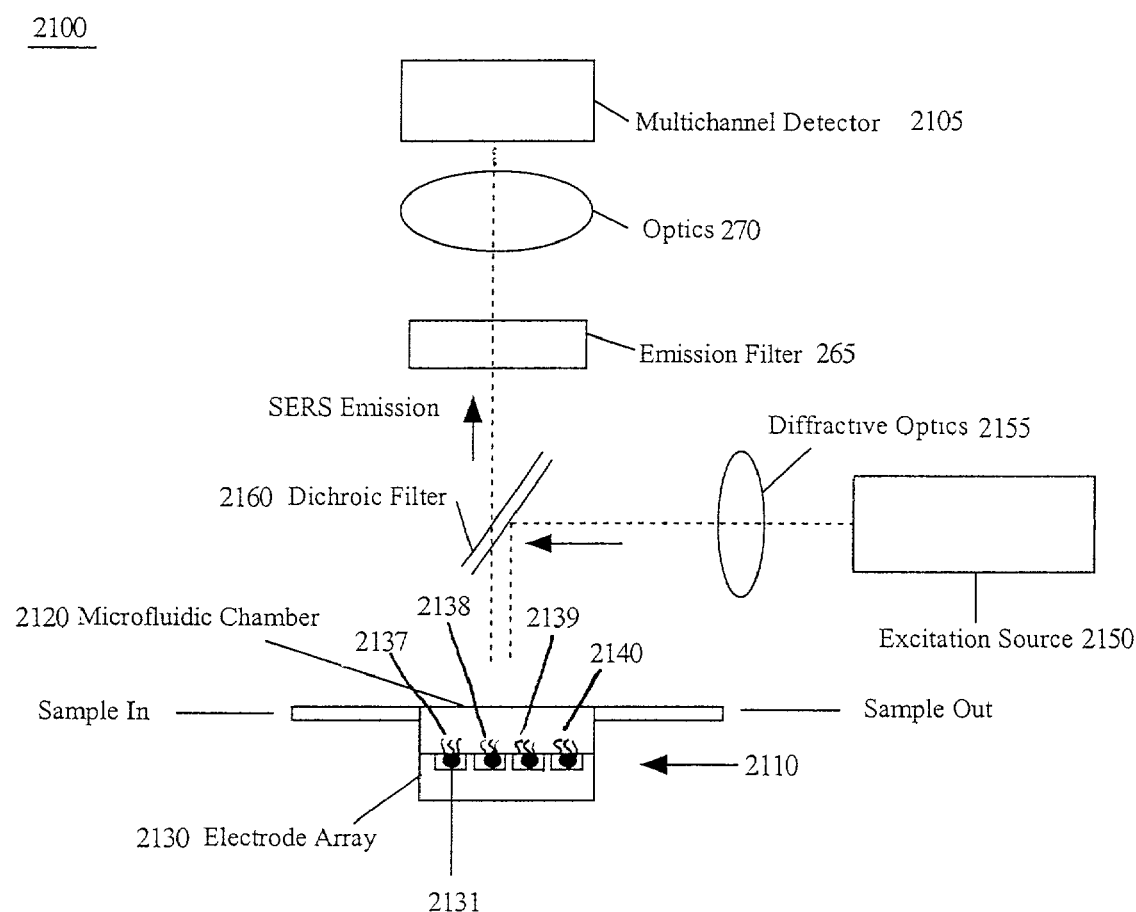
FIG. 21 illustrates a RASERS biochip system including an external optical detector.

To demonstrate the feasibility of the RASERS concept, a RASERS based-system 2100 with external optical detection illustrated in FIG. 21 was configured and tested. System 2100 included RASER chip 2110, RASER chip 2110 including microelectrode array 2130 comprising 16 microelectrode array elements 2131. Microelectrode control system (not shown) including a potentiostat for controlling bias voltage which was applied to provided to respective microelectrodes 2131. DNA based receptor probes 2137-2140 were disposed on array elements 2131 of microelectrode array 2130.

A microfluidics system including microfluidics chamber 2120 was provided including a microfluidics controller (not shown) was provided to supply analyte containing samples to and from receptor probes 2137-2140.

Excitation source 2150 provided light which was processed and directed by diffractive optics 2155 and dichroic filter 2160 to receptor probes 2137-2140. SERS signal scattered by receptor probes 2137-2140 were transmitted by dichroic filter 260 which were then processed by emission filter 265 and diffractive optics 270 before being detected by optical detector 2105.

Results obtained indicated that the SERS signal detected by optical detector 2105 may be changed by altering the adsorption state of the analytes onto the microelectrodes by changing the voltage of the potentiostat. The result demonstrates the feasibility of the RASERS concept.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as described in the claims.

The literature citations cited above are incorporated by reference herein for the reasons cited in the above text.

I claim:

1. An integrated SERS sensor system for the detection of targets including biotargets, said system comprising:
    at least one sampling platform, said sampling platform having a plurality of mnicrostructured or nanostructured metal surfaces thereon;
    a plurality of receptor probes disposed on said sampling platform within a range of an enhanced local field emanating from said microstructured metal or nanostructured surfaces upon irradiation, said receptor probes adapted for binding with at least one target molecule, said receptor probes generating a SERS signal when combined with said target molecule responsive to electromagnetic radiation applied thereto
    at least one excitation source of electromagnetic radiation for producing an optical beam and structure for producing a plurality of optical beams from said optical beam, said plurality of optical beams irradiating for irradiating said plurality of receptor probes, and an integrated circuit-based detection chip optically aligned with said plurality of receptors, said detection system for detection of said SERS signal, wherein said detector chip comprises a plurality of separate detection channels, at least one of said plurality of detection channels being dedicated to each of said plurality of receptor probes, and at least one of an integrated signal amplification system and an integrated signal processing system disposed on said chip for each of said plurality of detection channels.

2. An integrated SEES sensor system for the detection of targets including biotargets, said system comprising:

a CMOS integrated circuit-based detection chip comprising a plurality of separate detection channels and at least one of an integrated signal amplification system and an integrated signal processing system disposed on said chip for each of said plurality of detection channels;

an optical filter disposed on top of and in contact with said chip;

at least one integrated sampling platform disposed on and in contact with said optical filter and said plurality of detection channels, said sampling platform comprising:

a substrate;

a plurality of microsiructured or nanostructured metal surfaces disposed on said substrate;

a plurality of receptor probes disposed on said sampling platform within a range of an enhanced local field emanating from said ruicrostructured or nanostructured metal surfaces upon irradiation, said receptor probes adapted for binding with at least one target molecule, said receptor probes generating a SERS signal when combined with said target molecule responsive to electromagnetic radiation applied thereto ,whereffl at least one of said plurality of detection channels are dedicated to each of said plurality of receptor probes; and at least one excitation source of electromagnetic radiation for producing an optical beam and structure for producing a plurality of optical beams from said optical beam, said plurality of optical beams for irradiating said plurality of receptor probes.

3. The system of claim 2, wherein said optical filter comprises a notch filter.

4. The system of claim 1, wherein said plurality of receptor probes comprise biomimetics selected from the group consisting of molecular imprint antibodies, DNA-based aptamers, PNA, cyclodextrixis and dendrimers.

5. The system of claim 1, wherein said sensor system further comprises a microfluidic system having a plurality of microfluidic channels, said microfluidic system for directing samples through said microfluidic channels to said plurality of receptor probes.

6. The method of claim 5, wherein said microfluidic system comprises at least one selected from the group consisting of a capillary electrophoresis array, a liquid chromatography array, a gas chromatography array, and a lab-on-a-chip system.

7. The system of claim 1, wherein said sampling platform comprises a tape, wherein said system further comprises a structure for translating said tape.

8. The system of claim 1, wherein at least one of said target and said plurality of receptor probes includes at least one SERS label.

9. The system of claim 8, wherein said SERS label comprises at least one selected from the group consisting of cresyl fast violet, cresyl blue violet, rhodamine-6G, para-aminobenzoic acid, phthalic acids, erythrosin and aminoacridine.

10. The system of claim 1, wherein said excitation source comprises at least one selected from the group consisting of a low pressure lamp, a light emitting diode, a diode array, a laser and a laser array.

11. The system of claim 1, wherein said excitation source is disposed on said chip.

12. The system of claim 1, wherein said excitation source is disposed off-chip.

13. The system of claim 1. wherein said integrated circuit detection chip comprises at least one photodetector.

14. The integrated circuit of claim 1, wherein said on-chip signal amplification system or said signal processing system further comprises a microprocessor.

15. A SEP-S sensor system for the detection of targets, comprising:

at least one randomly-addressable SERS (RASERS) platform, said RASERS platform including a microelectrode array having a plurality of array elements, said array elements each capable of being independently biased, said array elements having a plurality of microstructured or nanostructured metal surfaces;

a plurality of receptor probes disposed on said microelectrode array of said RASERS platform within a range of an enhanced local field emanating from said microstructured or nanostructured metal surfaces upon irradiation, and a bias voltage source electrically coupled to said plurality of array elements, wherein said receptor probes generate a Raman signal when combined with said target molecule responsive to electromagnetic radiation applied to said receptor/target combination, said Raman signal is modulated by a level of bias applied by said bias source to said array elements.

16. The system of claim 15, further comprising an integrated circuit based detection system communicably connected to said receptors, said detection system adapted for detection of said Raman signal.

17. The system of claim 15, further comprising a control system for controlling bias provided by said bias source to said plurality of array elements.

18. The system of claim 15, wherein said plurality of receptor probes comprise at least one selected from the group consisting of DNA, RNA, antibodies, proteins, enzymes, a cell or cell component, and biomimetics.

19. The system of claim 18, wherein said biomimetics are at least one selected from the group consisting of molecular imprint antibodies, DNA-based aptamers, PNA, cyclodextrins and dendrimers.

20. The system of claim 1, said plurality of receptors comprise at least one protein receptor and at least one nucleic acid receptor.

21. The system of claim 1, wherein said plurality of receptors comprise at least two receptors selected from the group consisting of a protein receptor, a nucleic acid receptor, a cellular or cellular component detector, and a biomimetic detector.

22. The system of claim 16, wherein said detection system comprises plurality of a separate detection channels, said plurality of detection channels being optically aligned with said plurality of receptors.

* * * * *